United States Patent
Lain et al.

(10) Patent No.: US 9,533,113 B2
(45) Date of Patent: *Jan. 3, 2017

(54) INTEGRATED PULMONARY INDEX FOR WEANING FROM MECHANICAL VENTILATION

(75) Inventors: David Lain, Easton, MD (US); Joshua Lewis Colman, Jerusalem (IL); Michal Ronen, Givat-Brenner (IL); Sharon Einav, Zur Hadassah (IL)

(73) Assignee: Oridion Medical 1987 Ltd., Jerusalem (IL)

( * ) Notice: Subject to any disclaimer, the term of this patent is extended or adjusted under 35 U.S.C. 154(b) by 1301 days.

This patent is subject to a terminal disclaimer.

(21) Appl. No.: 13/336,652

(22) Filed: Dec. 23, 2011

(65) Prior Publication Data
US 2012/0145152 A1    Jun. 14, 2012

Related U.S. Application Data

(63) Continuation of application No. PCT/IL2010/000511, filed on Jun. 24, 2010, and a continuation-in-part of (Continued)

(51) Int. Cl.
| | | |
|---|---|---|
| *A61B 5/08* | (2006.01) | |
| *A61M 16/00* | (2006.01) | |
| *G06F 19/00* | (2011.01) | |
| *A62B 9/00* | (2006.01) | |
| *A61B 5/083* | (2006.01) | |

(52) U.S. Cl.
CPC .......... *A61M 16/0051* (2013.01); *A61B 5/08* (2013.01); *G06F 19/34* (2013.01); *A61B 5/0836* (2013.01); *A61M 2016/0036* (2013.01); *A61M 2205/505* (2013.01); *A61M 2205/584* (2013.01); *A61M 2230/06* (2013.01); *A61M 2230/10* (2013.01); *A61M 2230/205* (2013.01);
(Continued)

(58) Field of Classification Search
None
See application file for complete search history.

(56) References Cited

U.S. PATENT DOCUMENTS 5,355,880 A * 10/1994 Thomas ............. A61B 5/02007
                                            128/925
8,412,655 B2 * 4/2013 Colman ........................ 706/16
(Continued)

FOREIGN PATENT DOCUMENTS

WO    2008/081449 A2    7/2008
WO    2009/063446 A2    5/2009

*Primary Examiner* — Patricia Mallari
*Assistant Examiner* — Karen Toth

(57) ABSTRACT

There is provided herein a system for weaning a patient from mechanical ventilation (MV), the system comprising a ventilation device and a controller comprising an interface module configured to receive two or more measured patient parameters, wherein at least one measured patient parameters parameter comprise a $CO_2$ related parameter, wherein said controller is further configured to compute an Integrated Pulmonary Index (IPI) value based on the two or more measured patient parameters and to provide a signal to the ventilation device, based on the computed IPI value, wherein said signal adjusts one or more weaning related parameters in said ventilation device.

24 Claims, 13 Drawing Sheets

Related U.S. Application Data application No. 12/521,754, filed as application No. PCT/IL2008/000016 on Jan. 3, 2008, application No. 13/336,652, which is a continuation-in-part of application No. 12/742,794, filed as application No. PCT/IL2008/000894 on Jun. 30, 2008, now Pat. No. 8,412,655, which is a continuation-in-part of application No. PCT/IL2007/001393, filed on Nov. 13, 2007.

(60) Provisional application No. 61/219,791, filed on Jun. 24, 2009, provisional application No. 60/878,405, filed on Jan. 4, 2007, provisional application No. 61/071,959, filed on May 28, 2008.

(52) U.S. Cl.
CPC ... *A61M 2230/30* (2013.01); *A61M 2230/432* (2013.01); *G06F 19/3431* (2013.01); *G06F 19/3481* (2013.01)

(56) References Cited

U.S. PATENT DOCUMENTS

| | | | |
|---|---|---|---|
| 2004/0040560 A1 | 3/2004 | Euliano | |
| 2005/0098178 A1* | 5/2005 | Banner | A61B 5/0205 128/204.23 |
| 2008/0230065 A1* | 9/2008 | Heinonen | A61M 16/0051 128/204.23 |
| 2008/0236582 A1* | 10/2008 | Tehrani | A61H 31/02 128/204.22 |
| 2012/0145152 A1 | 6/2012 | Lain | |

* cited by examiner

INTEGRATED PULMONARY INDEX FOR WEANING FROM MECHANICAL VENTILATION

RELATED APPLICATION DATA

This patent application is a continuation of International Application No. PCT/IL2010/000511, filed Jun. 24, 2010, which claims the benefit of U.S. Provisional Application No. 61/219,791, filed Jun. 24, 2009, and is also a continuation-in-part of U.S. patent application Ser. No. 12/521,754, filed Mar. 31, 2010, which is the U.S. National Stage of International Application No. PCT/IL2008/000016, filed Jan. 3, 2008, which claims the benefit of U.S. Provisional Patent Application No. 60/878,405, filed Jan. 4, 2007, and is also a continuation-in-part of U.S. patent application Ser. No. 12/742,794, filed Sep. 14, 2010, which is the U.S. National Stage of International Application No. PCT/IL2008/000894, filed Jun. 30, 2008, which claims the benefit of International Application No. PCT/IL2007/001393, filed Nov. 13, 2007 and of U.S. Provisional Application No. 61/071,959, filed May 28, 2008, the contents of each of which are incorporated herein in their entireties by reference thereto.

BACKGROUND

Patients are placed on mechanical ventilation for a variety of medical dysfunctions. These include such conditions as: pulmonary distress, chest trauma, cardiac failure, paralysis, neuromuscular failure, multiple organ failure, sepsis leading to pulmonary complications, post-operative management and other conditions. Mechanical ventilators are typically adapted to do two things, provide for ventilation and oxygenation. Ventilation generally includes delivering controlled minute ventilations using sets of tidal volumes and respiratory rates. This can be provided using set pressure or set volume of gas supplied under to the lung. Oxygenation is generally controlled by delivering a level of prescribed oxygen and or positive end expiratory pressure (PEEP) used to increase functional residual capacity (FRC).

Even though the ventilation technology is constantly improving, ventilator dependence is still a serious medical and economic problem. It is well known that severe and sometimes lethal complications may develop the longer a patient is on ventilator support. In addition, as ventilator therapy is provided in specialized and very expensive Intensive Care Unit environments, there is a need to minimize ventilator dependency. Weaning the patients from artificial ventilation is among the most difficult challenges of the regarding intensive care ventilation.

Prior art ventilator weaning monitoring methods are not efficient enough and are often depending on subjective impressions of clinical fatigue or distress and/or arterial blood gas derangements that of necessity measure failure after the failure has already developed. More modem monitoring techniques such as the ratio of Tidal Volume to Respiratory Rate are still relatively crude indices of weaning performance. Weaning from ventilator dependency is potentially hazardous due to unexpected precipitous ventilatory failure, and early warning by appropriate monitoring means is imperative for patient safety. Further, controlled stress of weakened respiratory muscles is imperative in order to recondition these muscles, but in addition to not over-stress these recovering muscles and therefore cause further damage. It is often difficult to safely define the proper degree of weaning stress clinically.

Moreover, when a caregiver (such as a doctor or a nurse) considers weaning a patient from a ventilation machine and/or wishes to monitor the progress of the weaning process, he or she has to take into consideration and often even analyze a great deal of patient related parameters (data). These various parameters may each have different units and occasionally, different units may be used for the same parameter. Moreover, the absolute values of the parameters may not always be intuitive for understanding/interpretation and neither are they linearly proportional to severity of the condition. In addition, some parameters may have different meanings as to the condition of the patient when increasing and/or when decreasing, that is, for some parameters, decrease in the value indicates improvement while with other parameters, decrease in value may indicate deterioration of the patient condition. Thus the complexity and multiplicity of parameters also add to the existing difficulty of weaning initiation and monitoring.

There is thus a need in the art for systems, devices and methods that would allow straightforward monitoring the constantly changing condition of a patient undergoing weaning from ventilation.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other advantages or improvements.

According to some embodiments, there is provided a device for weaning a patient from mechanical ventilation (MV), the device comprising a controller comprising an interface module configured to receive two or more measured patient parameters, wherein at least one measured patient parameters parameter comprise a $CO_2$ related parameter, wherein said controller is further configured to compute an Integrated Pulmonary Index (IPI) value based on the two or more measured patient parameters and to provide a signal to a ventilation device, based on the computed IPI value, wherein said signal adjusts one or more weaning related parameters in the ventilation device. In other words, the controller is configured to, based on the IPI, the IPI behavior over time and/or the IPI trend, adjusts one or more weaning related parameters in the ventilation device by providing signal(s) to the ventilation device to adjust one or more weaning related parameters.

By "adjust" or "adjusting" it is meant changing or maintaining any weaning related parameter in a ventilation device, including, but not limited to, setting the ventilation device in an on/off mode, decreasing/increasing volume/pressure, decreasing/increasing oxygenation, changing the level of support to the ventilation, allowing the patient to rest from the weaning attempts, changing the mode/program of weaning (for example, PEEP (positive end expiratory pressure), CPAP (Continuous Positive Airway Pressure), BiPAP (Bilevel Positive Airway Pressure) and SIMV (Synchronized Intermittent Mandatory Ventilation)), etc.

According to some embodiments, there is provided a system for weaning a patient from mechanical ventilation (MV), the system comprising a ventilation device and a controller comprising an interface module configured to receive two or more measured patient parameters, wherein at least one measured patient parameters parameter comprise a $CO_2$ related parameter, wherein said controller is further configured to compute an Integrated Pulmonary Index (IPI) value based on the two or more measured patient parameters and to provide a signal to said ventilation device, based on the computed IPI value, wherein the signal adjusts one or more weaning related parameters in said ventilation device.

The IPI may be computed by (a) characterizing a first measured patient parameter based on a comparison of the first measured patient parameter against a first reference value; (b) characterizing a second measured patient parameter based on a comparison of the second measured patient parameter against a second reference value; and (c) computing the index value based on values associated with each of the characterized first and second measured patient parameters, wherein a weighting factor applied to the value associated with the second characterized measured patient parameter is influenced by the characterization of the first measured patient parameter.

The one or more weaning related parameters may include: ventilation volume, ventilation pressure, supplemental oxygen, positive end expiratory pressure (PEEP) or any combination thereof.

Adjusting one or more weaning related parameters in the ventilation device may include reducing or stopping the mechanical ventilation if the IPI value is at or above a predetermined value or continuing or increasing the support of the mechanical ventilation if the IPI value is below the predetermined value.

Adjusting one or more weaning related parameters in said ventilation device may include reducing or stopping supplemental oxygenation if the IPI value is at or above a predetermined value or continuing or increasing the supplemental oxygenation if the IPI value is below the predetermined value.

Adjusting one or more weaning related parameters in the ventilation device may include reducing or stopping positive end expiratory pressure (PEEP) if the IPI value is at or above a predetermined value or continuing or adding PEEP if the IPI value is below the predetermined value.

The controller may further be configured to compute a trend of the IPI value and to provide a signal to said ventilation device, based on the trend of the IPI value, wherein said signal adjusts one or more weaning related parameters in said ventilation device. The controller may further be configured to compute a reliability index of the index-value. The controller may further be configured to provide a medical recommendation regarding weaning from the ventilation machine.

The system may further include a graphical displaying the IPI value and or the recommendation regarding weaning from the ventilation machine.

According to some embodiments, there is provided a method for weaning a patient from mechanical ventilation (MV), the method comprising computing an Integrated Pulmonary Index (IPI) value based on two or more measured patient parameters, wherein at least one measured patient parameters parameter comprise a $CO_2$ related parameter; and adjusting one or more weaning related parameters in a ventilation device based on the computed IPI value. The IPI is computed by (a) characterizing a first measured patient parameter based on a comparison of the first measured patient parameter against a first reference value; (b) characterizing a second measured patient parameter based on a comparison of the second measured patient parameter against a second reference value; and (c) computing the index value based on values associated with each of the characterized first and second measured patient parameters, wherein a weighting factor applied to the value associated with the second characterized measured patient parameter is influenced by the characterization of the first measured patient parameter.

The one or more weaning related parameters may include: ventilation volume, ventilation pressure, supplemental oxygen, positive end expiratory pressure (PEEP) or any combination thereof.

Adjusting one or more weaning related parameters in the ventilation device may include reducing or stopping the mechanical ventilation if the IPI value is at or above a predetermined value or continuing or increasing the support of the mechanical ventilation if the IPI value is below the predetermined value.

Adjusting one or more weaning related parameters in said ventilation device may include reducing or stopping supplemental oxygenation if the IPI value is at or above a predetermined value or continuing or increasing the supplemental oxygenation if the IPI value is below the predetermined value.

Adjusting one or more weaning related parameters in the ventilation device may include reducing or stopping positive end expiratory pressure (PEEP) if the IPI value is at or above a predetermined value or continuing or adding PEEP if the IPI value is below the predetermined value.

The IPI may be in the range of 1 to 10, wherein the higher the IPI value, the better the patient condition is. An increase in the IPI value may be indicative of a better chance a patient has for a successful weaning. An increase in the IPI value or stabilization thereof may be indicative of a successful weaning process. A decrease in the IPI value may be indicative of a deterioration of a patient's condition.

The IPI may be computed according to a medical significance of at least one of the parameters. The method may further include computing a trend of the IPI value and to adjust one or more weaning related parameters in the ventilation device, based on the trend of the IPI value. The method may further include computing a reliability index of the index-value. The method may further include providing a medical recommendation regarding weaning from a ventilation machine. The method may further include graphically displaying the IPI value.

Computing the IPI may include applying a fuzzy logic, a Bayesian network, a decision tree, a neural network, a radial base function, a linear regression model, a non-linear regression model, an expert system, or any combination thereof. Computing the IPI may include averaging measured patient parameters over a period of time. The period of time may be determined based on one or more patient characteristics, on the stability of one or more measured patient parameters, or both.

The two or more measured patient parameters may include a $CO_2$ related parameter and one or more measured patient parameters selected from the group consisting of: another $CO_2$ related parameter, respiration rate (RR), an $O_2$ related parameter, heart rate (HR), an electrocardiogram (ECG), an encephalogram (EEG), blood pressure, and spirometry. The $CO_2$ related parameter may include a $CO_2$ waveform related parameter, an expired air $CO_2$ concentration, respiratory rate or any combination thereof. The $CO_2$ waveform related parameter may include $EtCO_2$, changes in $EtCO_2$, a slope of the increase in the $CO_2$ concentration, a change in a slope of the increase in the $CO_2$ concentration, time to rise to a predetermined percentage of a maximum value of $CO_2$ concentration, a change in time to rise to a predetermined percentage of a maximum value of $CO_2$ concentration, an angle of rise to a predetermined percentage of a maximum value of $CO_2$ concentration, a change in an angle of rise to a predetermined percentage of a maximum value of $CO_2$ concentration, breath to breath correlation, breath to breath correlation, a $CO_2$ duty cycle, a change in $CO_2$ duty cycle or any combination thereof. Computing may include applying a learning process, wherein the learning process increases reliability of the index value. The learning process may include neural network methods, a support vector machine (SVM), genetic algorithms, simulated annealing, expectation-maximization (EM), case based reasoning, or any combination thereof. Computing the IPI may be based on the two or more measured patient parameters and on one or more patient characteristics. The one or more patient characteristics may include age, weight, gender, medical condition, medication, ventilation, oxygen supply, lab tests results, blood pressure, medical history, intubation or any combination thereof. The medical history may include smoking, heart disease, lung disease, sleep apnea, a pacemaker, or any combination thereof.

According to some embodiments, there is provided a method of generating an integrated pulmonary index value of a patient, which includes receiving two or more measured patient parameters, wherein at least one of the measured patient parameters originates from a pulmonary sensor; and computing the integrated pulmonary index value based on the two or more measured patient parameters.

According to some embodiments, computing the integrated pulmonary index may include applying a mathematical model reflecting medical expert considerations, literature, clinical data, medical experience or any combination thereof. Computing the integrated pulmonary index may include applying a fuzzy logic, a Bayesian network, a decision tree, a neural network, a radial base function, a linear regression model, a non-linear regression model, an expert system, or any combination thereof.

According to further embodiments, the measured patient parameters maybe averaged over a period of time. The period of time may be predetermined. The period of time is determined based on one or more patient characteristics, on the stability of one or more measured patient parameters, or both.

According to further embodiments, the two or more measured patient parameters may include respiration rate, a CO2 related parameter, an O2 related parameter, heart rate, an electrocardiogram (ECG), an encephalogram (EEG), blood pressure, spirometry or any combination thereof. The CO2 related parameter may include a CO2 waveform related parameter, an expired air CO2 concentration, respiratory rate or any combination thereof. The CO2 waveform related parameter may include EtCO2, changes in EtCO2, a slope of the increase in the CO2 concentration, a change in a slope of the increase in the CO2 concentration, time to rise to a predetermined percentage of a maximum value of CO2 concentration, a change in time to rise to a predetermined percentage of a maximum value of CO2 concentration, an angle of rise to a predetermined percentage of a maximum value of CO2 concentration, a change in an angle of rise to a predetermined percentage of a maximum value of CO2 concentration, breath to breath correlation, a change in breath to breath correlation, a CO2 duty cycle, a change in CO2 duty cycle, minute ventilation, a change in minute ventilation or any combination thereof.

According to additional embodiments, computing integrated pulmonary index value may include assigning a first value to a first measured patient parameter based on a comparison of the first measured patient parameter against a first reference value; assigning a second value to a second measured patient parameter based on a comparison of the second measured patient parameter against a second reference value; and generating the integrated pulmonary index value based on the first and the second assigned values, wherein a weighting factor applied to the second assigned value is influenced by the first assigned value.

According to further embodiments, assigning the first value, the second value or both comprises applying a mathematical model reflecting medical expert considerations, literature, clinical data, medical experience or any combination thereof. Assigning the first value, the second value or both may include applying a fuzzy logic, a Bayesian network, a decision tree, a neural network, a radial base function, a linear regression model, a non-linear regression model, an expert system, or any combination thereof.

According to additional embodiments, generating the integrated pulmonary index value includes applying a mathematical model reflecting medical expert considerations, literature, clinical data, medical experience or any combination thereof. Generating the integrated pulmonary index value may include applying a fuzzy logic, a bayesian network, a decision tree, a neural network, a radial base function, a linear regression model, a non-linear regression model, an expert system, or any combination thereof.

According to yet additional embodiments, the method may further include receiving a plurality of parameters.

According to yet additional embodiments, the method of generating an integrated pulmonary index value of a patient may further include applying a learning process, wherein the learning process increases reliability of the integrated pulmonary index value. The learning process comprises neural network methods, a support vector machine (SVM), genetic algorithms, simulated annealing, expectation-maximization (EM), case based reasoning, or any combination thereof.

According to additional embodiments, the method of generating an integrated pulmonary index value of a patient may further include receiving one or more patient characteristics; and computing the integrated pulmonary index value based on the two or more measured patient parameters and on one or more patient characteristics. The one or more patient characteristics may include age, weight, gender, medical condition, medication, ventilation, oxygen supply, lab tests results, blood pressure, medical history, intubation or any combination thereof. The medical history may include smoking, heart disease, lung disease, sleep apnea, a pacemaker, or any combination thereof.

According to further embodiments, the integrated pulmonary index value is in the range of 1 to 10. An increase in the integrated pulmonary index-value may be indicative of an improvement in the condition of the patient. A decrease in the integrated pulmonary index-value is indicative of a deterioration of the condition of the patient.

According to yet further embodiments, computing the integrated pulmonary index value further may further include taking into account a medical significance of at least one of the parameters.

According to additional embodiments, the method of generating an integrated pulmonary index value of a patient may further include computing a trend of the integrated pulmonary index-value. The method may further include computing a reliability index of the integrated pulmonary index-value. The method may further include providing a medical recommendation.

According to some embodiments, there is provided a method of computing an index value indicative of a condition of a patient, which includes receiving two or more measured patient parameters, wherein the measured patient parameters originate from one or more sensing devices; characterizing a first measured patient parameter based on a comparison of the first measured patient parameter against a first reference value; characterizing a second measured patient parameter based on a comparison of the second measured patient parameter against a second reference value; and computing the index value based on values associated with each of the characterized first and second measured patient parameters, wherein a weighting factor applied to the value associated with the second characterized measured patient parameter is influenced by the characterization of the first measured patient parameter.

According to additional embodiments, there is provided a method of computing an index value indicative of a condition of a patient, which includes receiving a set of measured patient parameters, wherein the set comprises at least a first and a second measured patient parameters and wherein at least one measured patient parameter originates from a sensing device; assigning a first value to the first measured patient parameter based on a comparison of the first measured patient parameter against a first reference value; assigning a second value to the second measured patient parameter based on a comparison of the second measured patient parameter against a second reference value; and generating the index value based on the first and the second assigned values, wherein a weighting factor applied to the second assigned value is influenced by the first assigned value.

According to additional embodiments, the method may further include assigning a third value to a third measured patient parameter based on a comparison of the third measured patient parameter against a third reference value; and generating the index value based on the first, the second and the third assigned values, wherein a weighting factor applied to the second assigned value is influenced by the first assigned value and the third assigned value.

According to yet further embodiments, there is provided a method of computing an index value indicative of a condition of a patient, which includes receiving a set of measured patient parameters, wherein the set comprises at least two measured patient parameters and wherein at least one measured patient parameter originates from a sensing device; assigning a value to each of the at least two measured patient parameters based on a comparison of the measured patient parameters against one or more reference values; and generating the index value based on the assigned values, wherein a weighting factor applied to at least one of the assigned values is influenced by one or more assigned values.

According to some embodiments, there is further provided a method of computing an index value indicative of a condition of a patient, which includes receiving a set of measured patient parameters, wherein the set comprising at least two measured patient parameters and wherein at least one measured patient parameter originates from a sensing device; assigning a value to each of the at least two measured patient parameters based on a comparison of the measured patient parameters against one or more reference values, wherein at least one reference value is influenced by one or more assigned values; and generating the index value based on the assigned values.

According to some embodiments, computing the index value may include applying a mathematical model reflecting medical expert considerations, literature, clinical data, medical experience or any combination thereof. Computing the index may include applying a fuzzy logic, a Bayesian network, a decision tree, a neural network, a radial base function, a linear regression model, a non-linear regression model, an expert system, or any combination thereof.

According to some embodiments, the measured patient parameters may be averaged over a period of time. The period of time may be predetermined. The period of time may be determined based on one or more patient characteristics, on the stability of one or more measured patient parameters, or both.

According to some embodiments, the two or more measured patient parameters may include respiration rate, a CO2 related parameter, an O2 related parameter, heart rate, an electrocardiogram (ECG), an encephalogram (EEG), blood pressure, spirometry, or any combination thereof. The CO2 related parameter comprises a CO2 waveform related parameter, an expired air CO2 concentration, respiratory rate or any combination thereof. The CO2 waveform related parameter comprises EtCO2, changes in EtCO2, a slope of the increase in the CO2 concentration, a change in a slope of the increase in the CO2 concentration, time to rise to a predetermined percentage of a maximum value of CO2 concentration, a change in time to rise to a predetermined percentage of a maximum value of CO2 concentration, an angle of rise to a predetermined percentage of a maximum value of CO2 concentration, a change in an angle of rise to a predetermined percentage of a maximum value of CO2 concentration, breath to breath correlation, a change in breath to breath correlation, a CO2 duty cycle, a change in CO2 duty cycle, or any combination thereof.

According to some embodiments, the method of computing an index value may further include applying a learning process, wherein the learning process increases reliability of the index value. The learning process comprises neural network methods, support vector machine (SVM), genetic algorithms, simulated annealing, expectation-maximization (EM), case based reasoning, or any combination thereof.

According to some embodiments, the method of computing an index value may further include receiving one or more patient characteristics; and computing the index value based on the two or more measured patient parameters and on one or more patient characteristics. The one or more patient characteristics may include age, weight, gender, medical condition, medication, ventilation, oxygen supply, lab tests results, blood pressure, medical history, intubation or any combination thereof. The medical history may include smoking, heart disease, lung disease, sleep apnea, a pacemaker, or any combination thereof.

According to some embodiments, the index-value may be in the range of 1 to 10. An increase in the index-value may be indicative of an improvement in the condition of the patient. A decrease in the index-value may be indicative of a deterioration in the condition of the patient.

According to some embodiments, computing the index value may further include taking into account a medical significance of at least one of the parameters.

According to some embodiments, the method of computing an index value may further include computing a trend of the index-value. The method may further include computing a reliability index of the index-value. The method may further include providing a medical recommendation.

According to additional embodiments, there is provided an apparatus for generating an integrated pulmonary index value of a patient, said apparatus includes one or more ports for receiving two or more measured patient parameters, wherein at least one of the measured patient parameters originates from a pulmonary sensor; and a processing logic adapted to compute the integrated pulmonary index value based on the two or more measured patient parameters.

According to some embodiments, the processing logic may be adapted to apply a mathematical model reflecting medical expert considerations, literature, clinical data, medical experience or any combination thereof. The processing logic may be adapted to apply a fuzzy logic, a Bayesian network, a decision tree, a neural network, a radial base function, a linear regression model, a non-linear regression model, an expert system, or any combination thereof.

According to further embodiments, the processing logic may further be adapted to average measured patient parameters over a period of time. The period of time may be predetermined. The period of time is determined based on one or more patient characteristics, on the stability of one or more measured patient parameters, or both.

According to additional embodiments, the two or more measured patient parameters may include respiration rate, a CO2 related parameter, an O2 related parameter, heart rate, an electrocardiogram (ECG), an encephalogram (EEG), blood pressure, spirometry, or any combination thereof. The CO2 related parameter may include a CO2 waveform related parameter, an expired air CO2 concentration, respiratory rate or any combination thereof. The CO2 waveform related parameter may include EtCO2, changes in EtCO2, a slope of the increase in the CO2 concentration, a change in a slope of the increase in the CO2 concentration, time to rise to a predetermined percentage of a maximum value of CO2 concentration, a change in time to rise to a predetermined percentage of a maximum value of CO2 concentration, an angle of rise to a predetermined percentage of a maximum value of CO2 concentration, a change in an angle of rise to a predetermined percentage of a maximum value of CO2 concentration, breath to breath correlation, breath to breath correlation, a CO2 duty cycle, a change in CO2 duty cycle or any combination thereof.

According to additional embodiments, the processing logic may be adapted to compute the integrated pulmonary index value by characterizing a first measured patient parameter based on a comparison of the first measured patient parameter against a first reference value; characterizing a second measured patient parameter based on a comparison of the second measured patient parameter against a second reference value; and generating the integrated pulmonary index value based on values associated with each of the characterized first and second measured patient parameters, wherein a weighting factor applied to the value associated with the second characterized measured patient parameter is influenced by the characterization of the first measured patient parameter.

According to further embodiments, the processing logic may be adapted to apply a learning process, wherein the learning process increases reliability of the integrated pulmonary index value. The learning process may include neural network methods, a support vector machine (SVM), genetic algorithms, simulated annealing, expectation-maximization (EM), case based reasoning, or any combination thereof.

According to additional embodiments, the processing logic may further adapted to compute the integrated pulmonary index value based on the two or more measured patient parameters and on one or more patient characteristics. The one or more patient characteristics may include age, weight, gender, medical condition, medication, ventilation, oxygen supply, lab tests results, blood pressure, medical history, intubation or any combination thereof. The medical history may include smoking, heart disease, lung disease, sleep apnea, a pacemaker, or any combination thereof.

According to further embodiments, the integrated pulmonary index-value may be in the range of 1 to 10. An increase in the integrated pulmonary index-value may be indicative of an improvement in the condition of the patient. A decrease in the integrated pulmonary index-value may be indicative of a deterioration in the condition of the patient.

According to further embodiments, the processing logic may be further adapted to compute the integrated pulmonary index value according to a medical significance of at least one of the parameters. The processing logic may be further adapted to compute a trend of the integrated pulmonary index-value. The processing logic is further adapted to compute a reliability index of the integrated pulmonary index-value. The processing logic is further adapted to provide a medical recommendation.

According to some embodiments, there is provided an apparatus for generating an index value indicative of a condition of a patient, said apparatus include a port adapted to receive two or more measured patient parameters, wherein the measured patient parameters originate from one or more sensing devices; and processing logic adapted to: (a) characterize a first measured patient parameter based on a comparison of the first measured patient parameter against a first reference value; (b) characterize a second measured patient parameter based on a comparison of the second measured patient parameter against a second reference value; and (c) computing the index value based on values associated with each of the characterized first and second measured patient parameters, wherein a weighting factor applied to the value associated with the second characterized measured patient parameter is influenced by the characterization of the first measured patient parameter.

According to additional embodiments, the processing logic may be adapted to apply a mathematical model reflecting medical expert considerations, literature, clinical data, medical experience or any combination thereof. The processing logic may be adapted to apply a fuzzy logic, a Bayesian network, a decision tree, a neural network, a radial base function, a linear regression model, a non-linear regression model, an expert system, or any combination thereof.

According to further embodiments, the processing logic may be adapted to average measured patient parameters over a period of time. The period of time is predetermined. The period of time is determined based on one or more patient characteristics, on the stability of one or more measured patient parameters, or both.

According to some embodiments, the two or more measured patient parameters may include respiration rate, a CO2 related parameter, an O2 related parameter, heart rate, an electrocardiogram (ECG), an encephalogram (EEG), blood pressure, spirometry, or any combination thereof. The CO2 related parameter may include a CO2 waveform related parameter, an expired air CO2 concentration, respiratory rate or any combination thereof. The CO2 waveform related parameter may include EtCO2, changes in EtCO2, a slope of the increase in the CO2 concentration, a change in a slope of the increase in the CO2 concentration, time to rise to a predetermined percentage of a maximum value of CO2 concentration, a change in time to rise to a predetermined percentage of a maximum value of CO2 concentration, an angle of rise to a predetermined percentage of a maximum value of CO2 concentration, a change in an angle of rise to a predetermined percentage of a maximum value of CO2 concentration, breath to breath correlation, breath to breath correlation, a CO2 duty cycle, a change in CO2 duty cycle or any combination thereof.

According to further embodiments, the processing logic may be adapted to apply a learning process, wherein the learning process increases reliability of the integrated pulmonary index value. The learning process may include neural network methods, a support vector machine (SVM), genetic algorithms, simulated annealing, expectation-maximization (EM), case based reasoning, or any combination thereof.

According to additional embodiments, the processing logic may further be adapted to compute the integrated pulmonary index value based on the two or more measured patient parameters and on one or more patient characteristics. The one or more patient characteristics may include age, weight, gender, medical condition, medication, ventilation, oxygen supply, lab tests results, blood pressure, medical history, intubation or any combination thereof. The medical history may include smoking, heart disease, lung disease, sleep apnea, a pacemaker, or any combination thereof.

According to further embodiments, the index-value may be in the range of 1 to 10. An increase in the index-value may be indicative of an improvement in the condition of the patient. A decrease in the index-value may be indicative of a deterioration in the condition of the patient.

According to further embodiments, the processing logic may be further adapted to compute the index value according to a medical significance of at least one of the parameters. The processing logic may be further adapted to compute a trend of the index-value. The processing logic is further adapted to compute a reliability index of the index-value. The processing logic is further adapted to provide a medical recommendation.

In addition to the exemplary aspects and embodiments described above, further aspects and embodiments will become apparent by reference to the figures and by study of the following detailed descriptions.

BRIEF DESCRIPTION OF THE FIGURES

FIG. 1B—A graph depicting the respiration rate medical significance level;

FIG. 1C—A graph depicting the $SpO_2$ medical significance level;

FIG. 1D—A graph depicting the heart rate medical significance level;

DETAILED DESCRIPTION

Figure 1A:
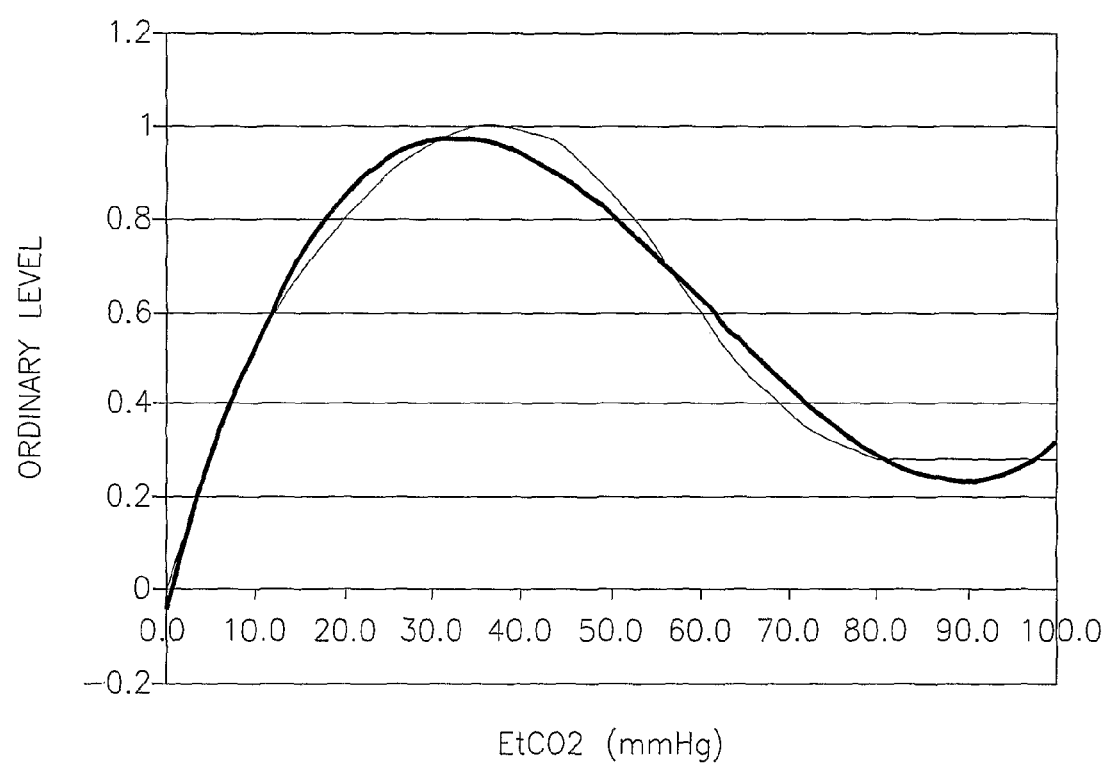
FIG. 1A—A graph depicting the $CO_2$ medical significance level.

In the following description, various aspects of the invention will be described. For the purpose of explanation, specific configurations and details are set forth in order to provide a thorough understanding of the invention. However, it will also be apparent to one skilled in the art that the invention may be practiced without specific details being presented herein. Furthermore, well-known features may be omitted or simplified in order not to obscure the invention.

As referred to herein, the terms "user", "medical user", "health care provider" and "health care professional" may interchangeably be used. The terms may include any health care provider who may treat and/or attend to a patient. A user may include, for example, a nurse, respiratory therapist, physician, anesthesiologist, and the like, however, a user may also include a patient.

As referred to herein, the terms "device", "monitoring device" and "medical device" may interchangeably be used.

As referred to herein, the terms "patient" and "subject" may interchangeably be used and may relate to a subject being monitored by any monitoring device for any physical-condition related parameter and/or health related parameter.

As referred to herein, the terms ordinary, normal, typical, standard and common may interchangeably be used.

As referred to herein, the terms "condition-index-value", "health index" and "index value" may interchangeably be used.

As referred to herein, the term "pulmonary" includes relating to, affecting, or occurring in the lungs.

As referred to herein, the term "respiratory" relates to the system that consists of or includes the airways, the lungs, and the respiratory muscles that mediate the movement of air into and out of the body.

As referred herein, the term "ventilatory" relates to ventilation (physiology), the movement of air into and outside the body.

According to some embodiments, the term "measured patient parameter/s" (such as a first, a second and/or any other measured patient parameter) may refer to any measurable or sensed parameter relating to a patient, such as, for example, but limited to: breath related parmeters, such as, for example, respiratory rate, CO2 related parameters, and the like; $O_2$ related parameters, such as, for example, SpO2, $O_2$ saturation, and the like; heart related parameters, such as, for example, heart rate, ECG, blood pressure, and the like; neurological parameters, such as, for example, EEG; spirometry related parameters, such as, for example, FEV1, FVC, and the like; and the like.

According to some embodiments, the term "reference value" (such as a first, a second and/or any other reference value) may include a value, a range of values or may be defining a portion of a range of values. The term "reference value" may refer, for example, to a value, a range of values or may be defining a portion of a range of values representing a normal (healthy) condition.

According to some embodiments, the term "pulmonary index value" or "Integrated Pulmonary Index value" may refer to a pulmonary index and/or a respiratory index. The term "pulmonary index value" or "Integrated Pulmonary Index value" may further relate to a respiratory and cardiac index and/or to a pulmonary and cardiac index.

According to some embodiments, the term "pulmonary sensor" may include any device, sensor, system, or the like, adapted to obtain, determine, sense and/or measure a pulmonary and/or respiratory related parameter, such as a capnograph, spirometer, flow meter, oximeter, an acoustic measurement device, or any combination thereof.

According to some embodiments, the terms "calculated" and "computed" may interchangeably be used.

Currently, in most health care settings, patient related parameters (data) are collected on line (or by other means) and may provide various health care providers, such as a nurse, a physician, a respiratory therapist, an anesthesiologist and the like, with information regarding the patient's status. The information routinely presented may include various types of information regarding various parameters that may be sensed by various sensors. Viewing and interpreting the information presented may sometimes be a cumbersome, complicated and time consuming task for the health care provider. More specifically, when a caregiver (such as a doctor or a nurse) considers weaning a patient from a ventilation machine and/or wishes to monitor the progress of the weaning process, he or she has to take into consideration and often even analyze a great deal of patient related parameters (data). These various parameters may each have different units and occasionally, different units may be used for the same parameter. Moreover, the absolute values of the parameters may not always be intuitive for understanding/interpretation and neither are they linearly proportional to severity of the condition. In addition, some parameters may have different meanings as to the condition of the patient when increasing and/or when decreasing, that is, for some parameters, decrease in the value indicates improvement while with other parameters, decrease in value may indicate deterioration of the patient condition. Thus the complexity and multiplicity of parameters also add to the existing difficulty of weaning initiation and monitoring.

There is thus provided, according to some embodiments of the invention, a method for weaning a patient from mechanical ventilation (MV), the method comprising computing an Integrated Pulmonary Index (IPI) value based on two or more measured patient parameters of the subject, wherein at least one measured patient parameters parameter comprise a CO2 related parameter, and determining one or more weaning related parameters based on the computed IPI value.

The Integrated Pulmonary Index (IPI), according to some embodiments of the invention, may monitor ventilation and oxygenation. The IPI calculates a single index value using values taken from ventilation, respiratory rate and a component of ventilation, a by-product of metabolism, end tidal carbon dioxide (etCO2), oxygenation, saturation of pulse oxygen (SpO2) heart rate (HR) taken from the pulse, for example, and other values. According to some embodiments of the invention, the IPI may be considered as representing a common denominator for some or all pulmonary or cardiopulmonary outputs and derives a single index that has been associated with levels of health. For example, in the IPI the level 10 is best and the level 1 is worst.

According to some embodiments of the invention the IPI may be used as an indicator of the health of a patient and may be used to determine when a patient's condition is likely to support spontaneous respiration.

Weaning may be accomplished by reducing the support provided by a mechanical ventilator until a patient is able to spontaneously support respiration. Respiration can be further defined as external and internal. External respiration may refer to exchanging breathing gases, inhalation and exhalation, with the atmosphere. Internal respiration may refer to gas exchange at the tissue level—supplying tissue with oxygen and removing carbon dioxide, a by-product of metabolism. According to some embodiments of the invention IPI may provide an indication of how well internal and external respiration is functioning and thus provide an indication as to how well the weaning is progressing.

Weaning Mechanical Ventilation by Control of Minute Ventilation.

Mechanical ventilators generally provide a selectable level of the total ventilator support given to a patient over one minute. This is known as minute ventilation (VE). The support can be set using a range of modalities including: assist-control, control, synchronized intermittent mechanical ventilation, pressure control, pressure support, airway release mechanical ventilation (MV), variations on these modes and other modes. Minute ventilation is set to achieve a level of carbon dioxide clearance from the body. The higher the set VE, the greater the support is for carbon dioxide clearance.

As a patient's condition improves, VE set on the ventilator, independent of mode, can be reduced. This reduction in mechanical VE will require the patient to provide addition VE to maintain a carbon dioxide clearance level. The method of VE drive provided by the patient is determined by chemoreceptors in the body that responds to changes in ph of the blood that is associated with carbon dioxide. If the patient's overall homeostasis is improved the VE requirements of the patient are met. This means that the CO2 level is control as to not create respiratory acidosis or uncompensated respiratory acidosis. In the blood the CO2 combines with water to form H2CO3 which is acidotic. The greater the CO2 the greater the risk for respiratory acidosis.

As the VE requirements needed via MV decrease and a homeostatic condition is met the IPI will respond. For example, if VE from the MV(set) decreases and CO2 increases the IPI will recognize a change in the etCO2 and respond by decreasing the IPI score. This would suggest the patient is not likely to be weaned.

If, on the other hand, VE from the MV(set) decreases and CO2 is stable, the IPI will recognize no change in the etCO2 and show no change in the IPI score. This would suggest the patient is more likely to be weaned.

It is noted that the IPI may be calculated using, in addition to c, other parameters such as respiration rate (RR), an O2 related parameter (such as SpO2), heart rate, an electrocardiogram (ECG), an encephalogram (EEG), blood pressure, spirometry, any combination thereof and any other parameter(s).

The $CO_2$ related parameter may include $CO_2$ waveform related parameter, an expired air $CO_2$ concentration, respiratory rate or any combination thereof. The $CO_2$ waveform related parameter comprises $EtCO_2$, changes in $EtCO_2$, a slope of the increase in the $CO_2$ concentration, a change in a slope of the increase in the $CO_2$ concentration, time to rise to a predetermined percentage of a maximum value of $CO_2$ concentration, a change in time to rise to a predetermined percentage of a maximum value of $CO_2$ concentration, an angle of rise to a predetermined percentage of a maximum value of $CO_2$ concentration, a change in an angle of rise to a predetermined percentage of a maximum value of $CO_2$ concentration, breath to breath correlation, breath to breath correlation, a $CO_2$ duty cycle, a change in $CO_2$ duty cycle or any combination thereof.

The physician can order a decrease in the MV(set), the VE supplied by the MV. He or she can set the IPI level not to drop to a value lower than X (for example, 6 or 7) during the reduction of MV(set). If the patient can maintain a VE(total) (that is set by the MV and provided by the patient) the MV(set) can be further reduced. As long as the IPI does not drop below X (based on patients condition and history), the weaning process can continue.

For example, a patient is receiving a MV(set) VE of 10 lpm (litter per minute), using a tidal volume 1.0 liter, and a RR (respiration rate) of 10 bpm. The IPI score (value) is 8. The extubation requirement for a VE weaning (not considering oxygenation) is an IPI of 7. The physician orders a reduction of MV(set) to 8 lpm. The patient must maintain an IPI of 7 or greater to further advance the weaning procedure. If the patient is able of maintaining a VE of 10, however, the RR increases from 10 bpm to 20 bpm, regardless of etCO2, the IPI will recognize the change in RR and lower the IPI accordingly. This would suggest, despite the adequate VE, that the patient is not ready to wean or that the weaning trial should be supported, for example, with PS (pressure support) to offset the breathing resistance of the ventilator circuit. In either circumstance, the IPI may alert the caregiver than an intervention is needed. With the appropriate response the patient will avoid a condition that could lead to further respiratory demands to meet VE requirements and could help avoid respiratory fatigue and depression.

An example of a successful weaning process is where the MV(set) is decreased and the VE is met without overburdening the respiratory system (increasing WOB (work of breathing)), and etCO2 is maintained, RR is controlled, and IPI remains in the selected range appropriate for continuing the weaning process.

Weaning by Oxygenation.

Supplemental oxygen is often provided during MV. The increased FiO2 (fraction of inspired oxygen in a gas mixture) helps prevent tissue hypoxia. The effect of FiO2 is measured with the SpO2 and is used in the IPI to determine overall fitness of the cardiopulmonary system. When tissue oxygenation is inadequate HR can increase in an attempt to circulate the blood faster to the tissue. According to some embodiments of the invention, this can also be measured by the IPI. It is noteworthy that in conditions of increasing cardiac load the oxygen consumption increases and so does CO2 production—both can be measured with the IPI indirectly by EtCO2/RR and SpO2/HR.

During weaning, maneuvers such as reducing FiO2 can be ordered by the physician. As FiO2 decreases and SpO2 remains adequate the IPI remains stable. If SpO2 drops then the IPI will have a corresponding drop. This would indicate that the weaning should be halted or slowed.

Another method to improve oxygenation is by adding positive end expiratory pressure (PEEP). The PEEP increases the surface area of the lung by recruiting alveoli, therefore increasing FRC. Selecting an IPI threshold and reducing PEEP as long as the IPI threshold is not crossed can reduce the PEEP.

For example, a FiO2 is set at 60%. The physician orders to reduce the FiO2 by 10% per hours without the IPI dropping to below 7, until a FiO2 of 35% is reached. Or the physician can order a PEEP of 15 cmH2O; dropped by 5 cmH2O per hour as long as a corresponding IPI level is maintained.

The IPI will respond faster to oxygen weaning than a single parameter.

Weaning Methods Choice with IPI

A physician may select to reduce FiO2 or PEEP before he or she begins decreasing the MV(set). In other cases the MV(set) may be a caregiver's first choice based on adequate oxygenation, such as in post-operative weaning where the VE(total) is inadequate until anesthetic agents impact is reversed. It is noted that the general anesthesia may cause decreased breathing and not necessarily a pulmonary conditions.

According to some embodiments, the IPI can be used manually inline with a MV. According to alternative or additive embodiments, the IPI can be built into a MV with protocols for weaning in place or selectable based on a patients needs. The IPI may be considered as a new method to wean by any weaning method. IPI may be considered as the common denominator for all weaning protocols. It is unlike spontaneous breathing trials in that it provide an objective measure of weaning regardless of the method or test for weaning.

According to some embodiments, there is a need to analyze the various patient related parameters (data) that are collected on line, in real time, and provide the health care providers with a more comprehensive, comprehensible, meaningful, intuitive, clearer and useful information about the patient's status. The data collected may be determined/calculated/computed and the information to the health care provider may be provided in the form of a condition-index-value that is directly related to the clinical condition of the patient. The condition-index-value may be determined/calculated/computed based upon various parameters of a patient that may be sensed/measured by appropriate sensors. The various parameters, according to which the condition index value is determined, may each have different units and occasionally, different units may be used for the same parameter. Moreover, the absolute values of the parameters may not always be intuitive for understanding/interpretation and neither are they linearly proportional to severity of the condition. In addition, some parameters may have different meanings as to the condition of the patient when increasing and/or when decreasing, that is, for some parameters, decrease in the value indicates improvement while with other parameters, decrease in value may indicate deterioration of the patient condition. This further demonstrate the importance of a condition index value, which integrates various parameters that may be measured in different units and may have different meanings into one comprehensible index value, which may be indicative of the absolute patient condition. Providing the condition-index value to the health care provider may result in a clear indication for the health care provider to realize when more medical attention is required for a given patient and for a given patient's condition. Since the condition-index value and the indications resulting therefrom may be deduced from several parameters, the sensitivity of monitoring the patient's condition may be increased, and earlier warnings with earlier intervention may be anticipated.

According to further embodiments, the condition-index-value may be determined/calculated/computed/determined by a device, such as, for example, a monitoring device. The monitoring device may include one or more sensors that may be used to sense and/or measure, and/or calculate and/or determine various health related parameters. The monitoring device may include any known medical monitoring device, such as, for example, capnograph, oxymeter, spirometer, heart rate sensors, blood pressure sensors, ECG, EEG, Ultrasound, and the like, and/or any combination thereof. Based on the various measurements, the device may calculate the condition-index-value, and display the index alone or in combination with the various patient parameters that may be sensed/measured by appropriate sensors. In addition, the device may also provide medical recommendations to the user based on the analysis of the collected patient data. Moreover, the device may track and notify the health care provider regarding changes over time of the patient's condition. For example, the device may notify the health care provider if the patient's condition is stable, improving or deteriorating.

According to some embodiments, the condition-index-value may be a unit-less value in any predetermined range, such as, for example, in the range of 1 to 100. For example, condition-index-value may in the range of 1 to 10, wherein 10 indicates the best condition, and 1 indicates the worst condition. Within the range of 1 to 10, sub ranges (subdivisions) may be assigned. For example, a sub-range from 8 to 10 may be indicative of a stable, normal condition, where no intervention is needed. A sub-range of 6-7 may be indicative to the health care provider that more attention is needed patient re-evaluation is recommended. A sub range of below 5 may indicate to the health care provider that intervention is needed and patient re-evaluation may be necessary. In addition, the various sub-ranges of the condition-index-value may be assigned different graphical signs, when displayed to the health care provider. The different graphical signs may include, for example, different colors, different units, different letters, and the like. For example, for condition-index-value in the sub-range of 8 to 10, the value may be colored green, for condition-index-value in the sub-range of 5 to 7, the value may be colored yellow, and for condition-index-value in the sub-range of below 5, the value may be colored red. In addition, various other visual indicators may also be used to indicate changes that may be correlated with known physical conditions, such as, for example, up and down arrows that may indicate, for example, an increase or decrease, respectively, in one or more measured patient parameters.

According to some embodiments, the condition index value may be calculated by various means, such as, for example, by use of mathematical equations, algorithms, formulas, and the like, that may take into consideration one or more of the values or derivatives of the values of the parameters that are being measured by the monitoring device.

According to further embodiments, the change of the condition-index-value over time (referred to herein as condition-index-value trend) may be displayed graphically. The graphic display may exhibit the condition-index-value trended over the last "n" (time units) of monitoring. For example, n may be any time period in the range of 5 minutes to 12 hours. This display may be used to indicate the patient's status, such as, for example: stable, improving, deteriorating, as well as providing a depiction of the rate and change of the patient's status. Displaying of the condition-index-value trend may simplify the assessment of the changes in the condition of the patient as compared to assessing the patient condition based on the trend of the individual parameters. When looking at the trends of the individual parameters, it may not be easy and intuitive to determine the patient's status and change in status, without taking into consideration the absolute values of the individual parameters and their interactions.

According to further embodiments, the condition-index-value trend may be depicted as a graphic display of the condition-index-value over time. The duration period of the trend may be chosen to be over any time period in the range of, for example between 5 minutes to 12 hours of the last measurements. The resolution of the graphical display may change accordingly in correlation to the selected time period.

According to further embodiments, an index of reliability (referred to herein also as "reliability index" or "RI") may also be determined. The index of reliability may provide a measure of the reliability of the data and more specifically, the reliability of the condition-index-value. For example, the reliability index may be used to predict and anticipate artifacts. The reliability index may be determined, for example, by analysis of the $CO_2$ waveforms, as depicted by a capnogram. If breath flow is also measured, its waveforms may also be used for this purpose. The use of breath flow measurements may refine and improve the index of reliability. Breath flow waveforms strongly complement the waveforms created by the $CO_2$ measurement, since both measurements represent essentially the same event, which is the breath cycle. While the breath flow relates to the envelope of the waveform, the $CO_2$ relates to the $CO_2$ concentration within the envelope. Using both parameters may better reveal and uncover what is a measurement noise, artifact, and the like.

According to additional embodiments, a pause frequency parameter may be determined This parameter may include a measure of events wherein no breathing is detected, over a period of time. The events of lack of breathing may include, for example, pause and apnea events, and the pause frequency parameter may include a measure of a patient's pause and apnea events over a period of time. The pause frequency parameter may be determined/calculated from the $CO_2$ waveform, as obtained by the capnogram. A pause event may be defined, for example, as any inhalation stage that persists for longer than any number of seconds in the range of, for example, 5 to 40 seconds (such as for example 20 seconds), and proceeds after an exhalation period lasting less than any number of seconds in the range of, for example, 5 to 20 seconds (such as, for example, 10 seconds). The time periods may be determined, for example, according to the average time of the last three exhalation cycles. Such determination of a pause event may be used to exclude a slow, rhythmic breathing pattern from being defined as a group of pause events. In addition, a maximum time out of, for example, 100 seconds may be determined. If a pause is detected, a new pause can only be counted if at least three new, valid breath cycles were detected beforehand. Thus, the Pause Frequency Parameter may be defined by the number of pause events per period of time (such as, for example, an hour). The pause frequency may be updated at any time intervals, such as, for example, every 5 minutes, after the period of 1 hour. The values of the pause frequency may further be stored and used for the display of the pause frequency trend, wherein the trend data represent the change of the pause frequency over time. According to some exemplary embodiments, during the first hour (when insufficient data has accumulated), a value may be provided and updated, for example, every 15 minutes until 1 hour has been reached (wherein during this time period the frequency is determined/calculated as if it was determined/calculated for 1 hour). During this time period an indication showing that the pause frequency is still based on a shorter period than 1 hour may be displayed. Since the health care provider, such as a nurse, may not be constantly present next to the patient and/or the monitoring device, and may not constantly track (monitor) the patient condition, a parameter, such as the pause frequency parameter, which is a periodic type effect, may not easily be observed by the health care provider if not otherwise tracked by the monitoring device. In addition, according to further embodiments, the pause amplitude parameter may also be determined. The pause amplitude parameter may be determined by measurements of the time length (such as, for example, in the range of 5 to 60 seconds) of each of the detected pause events and the dispersion of the time lengths of the pause events over a period of time (such as, for example, over a time period of 60 minutes).

According to some embodiments, the device may further include and display medical recommendations to the health care professionals. The medical recommendations may be deduced from analysis of at least some of the individual parameter values and patterns and comparison of the measured values and patterns to the known ranges and patterns of the individual parameters. These recommendations may be displayed in addition to the indications derived from the determined/calculated condition-index-value.

According to some embodiments the medical device may include a user interface that may allow the user to select the data to be displayed and to control various operating parameters. Moreover, different displays may be included to accommodate different needs of the different users (such as a nurse, a physician, an anesthesiologist, and the like). Allowing the user to change the view of the data may permit the user to toggle through the different levels of information for further evaluation of a condition. For example, the basic screen may display the condition-index-value and the condition-index-value trend data. Changing to the next display may reveal the actual (measured) data values and the trends of the values that relate to the parameters from which the condition-index-value is determined/calculated. Further toggling the display may provide the pause frequency and other related analysis and calculation. The use of the various displays may also allow the user to focus on the parameters that caused an indication of an event and/or recommendation to the user.

According to further embodiments, the user interface may also allow the user to enter information that is characteristic for each patient. The use of characteristic patient information is necessary to allow accuracy of the various measurements and calculations. Such information may include, for example age, weight, height, sex, and the like, of the specific patient. In addition, classification detection means of various patients may be utilized, wherein the classification may be based on parameters such as, for example, age group, weight group, sex, and the like. Using such classification may allow the monitoring device to correct its settings to be appropriate for that relevant patient type and environment.

According to some exemplary embodiments, the condition-index-value may represent the respiratory status and/or the pulmonary status and/or the cardiac status of the patient. This may be accomplished by providing an index value that is determined/calculated based upon one or more of various respiratory, pulmonary and/or cardiac parameters, such as, for example, but not limited to: $CO_2$ related parameters; $O_2$ related parameters; $EtCO_2$; $CO_2$ waveform related parameters, such as, for example, changes in $ETCO_2$, $CO_2$ duty cycle, inhalation to exhalation ratio, a slope of the increase in the CO2 concentration, a change in a slope of the increase in the $CO_2$ concentration, time to rise to a predetermined percentage of a maximum value of $CO_2$ concentration, an angle of rise to a predetermined percentage of a maximum value of $CO_2$ concentration, breath to breath correlation, CAP-FEV1 (forced expiratory volume over 1 sec obtained from at least one capnographic measurement, a measure of flow), CAP-FEV1/FVC, and the like; an expired air $CO_2$ concentration; breathing related parameters; heart function related parameters; neurological parameters; systemic perfusion related parameters; visual parameters; FEV1 (forced expiratory volume over 1 sec, a measure of flow); FVC (forced vital capacity, a measure of volume); blood pressure; NI blood pressure; systolic to diastolic ratio; respiratory rate; breath flow rate; spirometry readings; $O_2$ saturation; $SpO_2$; blood pressure; blood gases; heart rate; Electrocardiogram (ECG); Electroencephalogram (EEG); Ultrasound measurements, such as heart echogram, and the like, or any combination thereof.

As referred to herein, the term $EtCO_2$ relates to End tidal $CO_2$. The $CO_2$ is exhaled out of the body and the concentration of the exhaled $CO_2$, also known as end tidal $CO_2$ ($EtCO_2$) is an approximate estimation of the alveolar $CO_2$ pressure and thus of the arterial levels of $CO_2$. The measurements of the $CO_2$ concentration in a breath cycle are performed by a capnograph, and the results are a numerical value displayed also in a graphical format in the shape of a waveform named a capnogram. The values of $EtCO_2$ may be measured in units of volume or pressure, such as, for example, mmHg As referred to herein, the term $SpO_2$ relates to the saturation of peripheral oxygen. It is a measurement of the amount of oxygen attached to the hemoglobin in red blood cells in the circulatory system. $SpO_2$ values are generally given as a percentage (for example, normal value is above 96%). $SpO_2$ may be monitored and measured by various monitors, such as, for example, a Pulse Oximeter.

As referred to herein, the term Respiration Rate (RR) is defined as the number of breaths taken in a minute, and it may change under various physiological and medical conditions. The rate may be abnormally high (tachypnea), abnormally low (bradypnea) or non-existent (apnea).

As referred to herein, the term Heart (Pulse) Rate (HR) relates to the number of heart pulses (beats) in a minute. Pulse rate is usually considered to be a combination of left ventricular stroke volume, ejection velocity, the relative compliance and capacity of the arterial system, and the pressure waves that result from the antegrade flow of blood and reflections of the arterial pressure pulse returning from the peripheral circulation, and some or all of which may be effected by $CO_2$. For example, in acute pulmonary edema secondary to left ventricular decompensation, there is frank respiratory failure. Also, the effect on the heart following drug administration, such as, for example, morphine, will lead to a fall in $_PO_2$ (partial $O_2$ pressure in blood) and a rise in $_PCO_2$ (partial pressure $CO_2$ in blood). Thus, heart rate may be used to indicate severity of respiratory/pulmonary status.

As referred to herein, the term "hypoventilation" relates to a state of respiratory depression that may occur when ventilation is inadequate to perform needed gas exchange. Hypoventilation may cause an increased concentration of carbon dioxide and respiratory acidosis. Hypoventilation may be caused by various medical conditions and/or by use of some drugs and medicines.

As referred to herein, the term "hyperventilation" relates to a state of breathing faster and/or deeper than necessary, thereby reducing the carbon dioxide concentration of the blood below normal.

According to some exemplary embodiments, the condition-index-value may be a Pulmonary/Respiratory Index value, also referred to herein as "PI" or "IPI" (Integrated Pulmonary Index). The PI index may represent a measurement of the patient's respiratory and/or pulmonary and/or cardiac status. It may be deduced from various measured patient parameters, such as, for example: $EtCO_2$, Respiration Rate, $SpO_2$ and Heart Rate. The individual parameters, according to which the PI is calculated, may each have different units, and occasionally, different units may be used for the same parameter, such as, for example, for $EtCO_2$ that can be defined in units of, for example, kPas, mmHg or Vol (percent). Moreover, the absolute values of the parameters may not always be intuitive for understanding/interpretation and neither are they linearly proportional to severity of the condition. In addition, some parameters may have different meanings as to the condition of the patient when increasing and/or when decreasing, that is, for some parameters, decrease in the value indicates improvement while with other parameters, decrease in value may indicate deterioration of the patient condition. These and other reasons, demonstrate the importance of a condition index value, such as the PI, which integrates various parameters that may be measured in different units and may have different meanings into one comprehensible index value, which may be indicative of the absolute patient condition in general and on the respiratory and/or pulmonary and/or cardiac condition of the patient in particular. The PI may be a unit-less value in the range of 1 to 10, wherein 10 indicates the best condition, and 1 indicate the worst condition. Within the range of 1 to 10, sub ranges (subdivisions) may be assigned. For example, a sub-range from 8 to 10 may be indicative of a stable, normal condition, where no intervention is needed. A sub-range of 6-7 may be indicative for the health care provider that more attention is needed. A sub range of below 5 may indicate to the health care provider that intervention and/or patient re-evaluation and/or a change in therapy is recommended. In addition, the various sub-ranges of the condition-index-value may be assigned different graphical signs, when displayed to the health care provider. The different graphical signs may include, for example, different colors, different units, different letters, and the like. For example, for condition-index-value in the sub-range of 8 to 10, the value may be colored green, for condition-index-value in the sub-range of 5 to 7, the value may be colored yellow and for condition-index-value in the sub-range of below 5, the value may be colored red. In addition, various other visual indicators may also be used to indicate changes that may be correlated with known medical conditions, such as, for example, up and down arrows that may indicate, for example a state of hyperventilation and hypoventilation, respectively.

According to some embodiments, the PI index value may be determined by various ways, using various calculation methods and various algorithms, as further detailed below herein. Generally, the PI may be deduced from various parameters and may be assigned the highest value, for example "10", when the individual values of the various parameters are well within their respective normal ranges. The PI value may decrease below "10" when the value of one or more of the individual parameters changes from the normal respective ranges for those parameters. The decrease of the PI value may be sharper when several individual parameters change together.

According to some embodiments, the PI value may be updated continuously, and it may be determined/calculated from an average of the values of the parameters that are used to produce the PI value. In addition, the averaging time used for the determination of the PI value may also be adaptive. For example, if there is an erratic measurement, the average time may increase. The erratic characteristics used for deciding the averaging time may result, for example, from the respiratory rate values, the $CO_2$ waveform, and any other suitable parameter that is used for the calculation of the PI.

According to further embodiments, the PI value may also be indicative of conditions such as hypoventilation and hyperventilation. When the PI is indicative of these conditions, an appropriate additional indicative signaling may be displayed, such as, for example, an upward arrow (indicative of hyperventilation) and downward arrow (indicative of hypoventilation). The decision as to whether the patient's status is in either hypoventilation or hyperventilation may be based, for example, upon the Respiratory Rate, when respiratory rate is one of the measured patient parameters.

According to some embodiments, there are various methods to calculate the PI value. Generally, various parameters may be measured and used for the calculation of the PI value. According to some exemplary embodiments, the PI may be determined/calculated based on measuring the values of at least one of the parameters: $EtCO_2$, Respiration Rate, $SpO_2$ and Heart Rate. The real time values of these parameters may be measured continuously. For example, an adaptive running average may be collected for all of the 4 measured patient parameters (average $EtCO_2$, average respiratory rate, average heart rate and average $SpO_2$). This adaptive running average may be determined/calculated by collecting the data displayed by the monitors that measure the parameters each second, and averaging over a period of time (as explained below). In this way, the determined/calculated average takes into consideration not only the values collected over the last "x" number of seconds, but also the length of time the value was displayed. The PI may then be determined/calculated using these average values. The averaging time period may be determined/calculated and defined using an adaptive type algorithm. For example, the default time period may be in the range of 5 to 60 seconds, such as, for example, 30 seconds. The time may increase in steps of, for example, 2 to 30 seconds, such as, for example, in steps of 15 seconds; and the maximum period of time may be in the range of 5 to 180 seconds, such as, for example, 90 seconds, 120 seconds, and the like. In order to evaluate if the data is stable or erratic, information that may be used to determine if averaging time is to be increased or decreased, respectively, the parameter value of respiratory rate may be used. The standard deviation of the respiratory rate over the last predetermined period of time (such as, for example, 30 seconds) may be continuously measured. If the standard deviation of the respiratory rate value is below a predefined threshold, then the averaging period does not change. If the standard deviation of the respiratory rate over the last predetermined period of time is above the predetermined threshold, then the averaging period may be increased (for example, by 15 seconds).

According to some embodiments, the PI may be determined/calculated by using mathematic calculations. The calculation may be based on the measuring the values of at least one of the parameters: $EtCO_2$, Respiration Rate (RR), $SpO_2$ and Heart Rate (HR), and the determined/calculated average of those parameters, as detailed hereinabove. The calculations may relay on known defined ranges values for each of the measured patient parameters (in correlation with the patient characteristics, as detailed below). Meeting predefined conditions of the various measured parameters values result in an appropriate determined/calculated PI value. For example, and as further detailed in Example 1, when the following conditions are realized, the PI may 10 or 9 and no arrows, indicative of changes in condition are displayed: If RR is >12 & <28 and $EtCO_2$ is ≥28 & <44 and $SpO_2$ is >94%, Then: PI=10. If RR is >12 & <28 and $EtCO_2$ is ≥28 & <44 and $SpO_2$>90% & <94%, Then: PI =9.

Figure 1B:
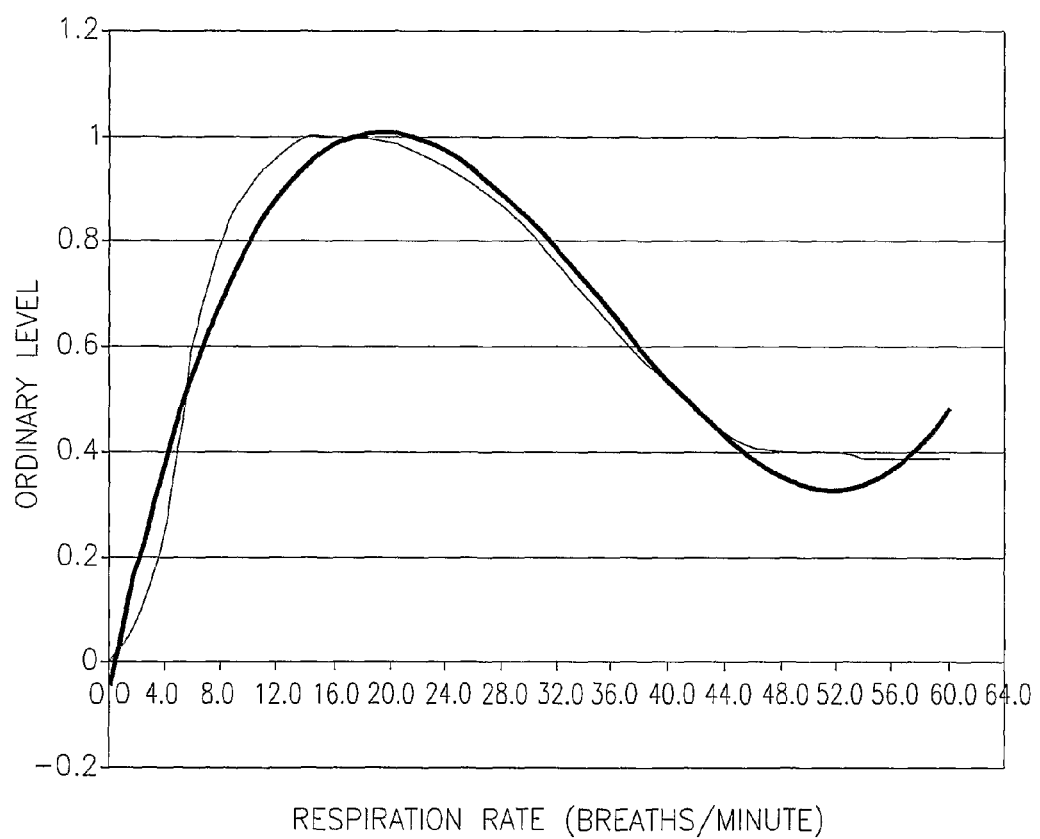
Figure 1C:
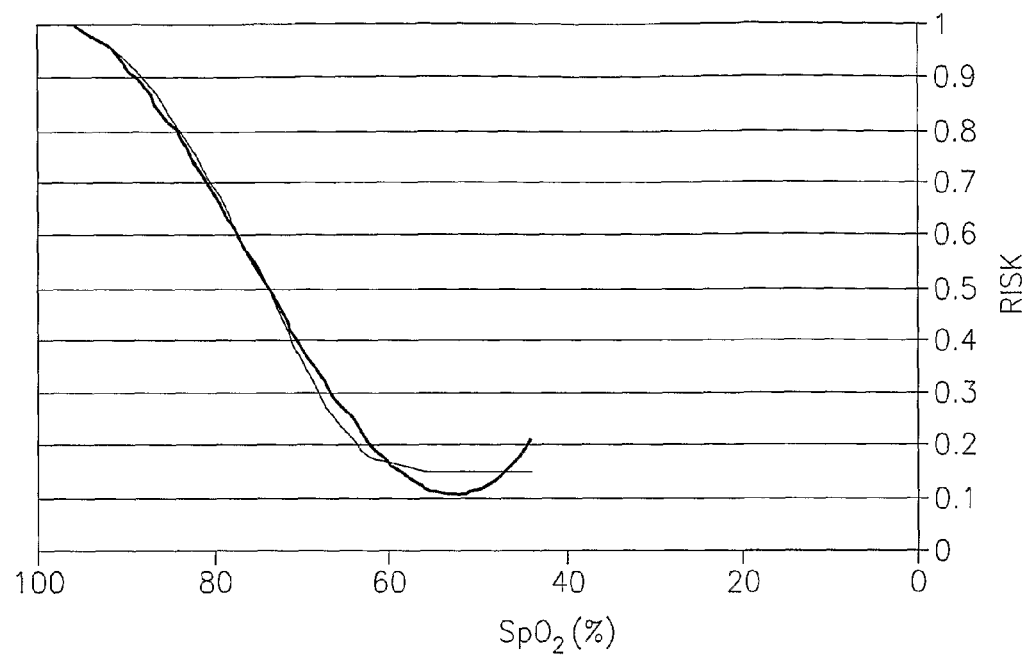
Figure 1D:
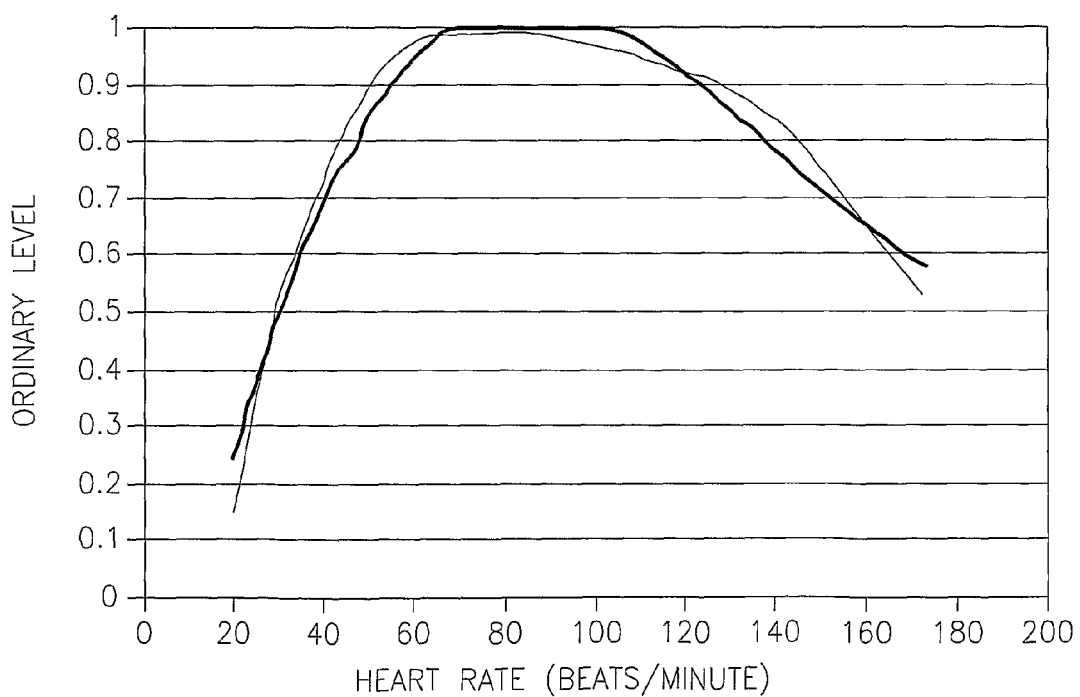

According to some embodiments, the PI may be determined/calculated by using mathematic calculations. The calculations may be based on multiplication of the medical significance level (risk/probability level) that is associated with each of the measured patient parameters. The medical significance level of each of the measured patient parameters may be determined by creating a graph, indexing tables, and the like, which correlate the value of the parameter with an ordinary (standard/typical, common/normal) level of a physical condition, such as, for example ventilatory condition (such as breathing, respiration, exhaling, inhaling). The ordinary level of the physical condition may be in the range of 0 to 1, wherein 1 signifies the best physical condition and 0 signifies the worse physical condition. Thus, for example, mathematical functions may be provided for each of the measured patient parameters, where the maximum value of 1 may relate to a physical condition that is normal, and a minimum value of 0 may relate to a physical condition that is worst, such as for example, when no ventilatory performance is detected at all. FIG. 1A illustrates a graph which depicts the medical significance (risk levels) of the $EtCO_2$ parameter. As shown in FIG. 1A, the Y-axis is the ordinary level, on the scale of 0 to 1. The X-axis is the level of $EtCO_2$ in units of mmHg. The medical significance curve depicts the correlation curve between the ordinary level and the level of $EtCO_2$ and the determined/calculated curve that best correlates to the medical significance curve. As can be deduced from the graph, at low EtCO2, the ordinary level value decreases to zero, indicative of moving towards apnea; at high EtCO2, although indicative of a dangerous condition (that may cause the blood to change its alkali level which may consequently many essential chemical processes), the ordinary level value does not fall to zero. The equation of the exemplary medical significance curve, which is illustrated in FIG. 1A may be described by the equation: $Y_1=8E-06x3-0.0015x2+0.0724x-0.0496$. FIG. 1B illustrates an exemplary graph which depicts the medical significance levels of the respiration rate parameter. As shown in FIG. 1B, the Y-axis is the ordinary level, on a scale of 0 to 1. The X-axis is the respiratory rate in units of number of breaths in a minute. The medical significance curve depicts the correlation curve between the ordinary level and respiratory rate and the determined/calculated curve that best correlates to the medical significance curve. The equation of the exemplary medical significance curve, which is illustrated in FIG. 1B, may be described by the equation: $Y_2=4E-05x3-0.0043x2+0.1231x-0.0378$. FIG. 1C illustrates an exemplary graph which depicts the medical significance levels of the $SpO_2$ parameter. As shown in FIG. 1C, the Y-axis is the ordinary level, on a scale of 0 to 1. The X-axis is the $SpO_2$ percentile. The medical significance curve depicts the correlation curve between the ordinary level and the $SpO_2$ and the determined/calculated curve that best correlates to the medical significance curve. The exemplary equation of the medical significance curve which is illustrated in FIG. 1C may be described by the equation: $Y_3=-2E-05x3+0.004x2-0.2778x+6.1214$. FIG. 1D illustrates an exemplary graph which depicts the medical significance levels of the heart rate parameter. As shown in FIG. 1D, the Y-axis is the ordinary level, on a scale of 0 to 1. The X-axis is the heart rate that is measured in number of beats in a minute. The medical significance curve depicts the correlation curve between the ordinary level and the heart rate and the determined/calculated curve that best correlates to the medical significance curve. The equation of the exemplary medical significance curve which is illustrated in FIG. 1D may be described by the equation: $Y_4=8E-07x3-0.0003x2+0.0406x-0.4389$. Similarly to creating and calculating the correlation equations, indexing tables may also be used to correlate between the ordinary level and the value of each of the measured patient parameters.

According to some embodiments, the PI may be determined/calculated by multiplying the medical significance factors of each of the measured patient parameters obtained by the equations detailed above herein, and multiplying the result by 10, to get an IP value in the range of 1 to 10. The equation may be described as: $PI=Y_1*Y_2*Y_3*Y_4$. According to some exemplary embodiments, the HR medical significance value ($Y_4$) is introduced to the calculations only if the medical significance value of one of the other parameters is less than 0.8. In addition, the equations presented hereinabove are valid up to the following maximal values of the individual parameters: the $EtCO_2$ value reaches a value of about 90 mmHg, the respiratory rate reaches a value of about 50 bpm and $SpO_2$ reaches 50%. Above or below these values a default value of 0.2 may be used.

According to additional embodiments, if the determined/calculated index is below 8, an upward arrow indication may be included if the respiration rate is greater than a predetermined number of beats per minute (BPM), such as, for example, 24 BPM. A downward arrow indication may be included if the respiration rate is below a predetermined number of BPM, such as, for example, 12 BPM. If the respiration rate is within a predetermined range, such as, for example between 12 and 24 BPM, no arrow indication is provided.

According to further embodiments, the PI may be determined/calculated by the use of various algorithms that may be used to create a mathematical model for the index that may reflect the "real time" assessment of a health care provider on the patient's pulmonary/respiratory status. In this respect, "real time" may be defined as being "in-time" for the health care provider to respond to a medical situation. "Real time" may be, for example, in the range of seconds (for example, 0 to 120 seconds), in the range of minutes (for example 1 to 10 minutes), and the like. Some of the requirements from such an algorithm or method are: to express correctly the consensus assessment of various health care providers, such as medical experts, physicians, nurses, and the like, wherein the consensus assessment may be determined by a weighted and/or un-weighted average. By weighted average, for example, a physician's assessment may be weighted more than that of a respiratory therapist. For example, by weighted average, each health care provider may "weight" their opinion, for example by adding a confidence value to their assessment; easy and flexible implementation of the algorithm (that is, simplify the fine-tuning of the mathematical models); and fast calculations. By implementing the algorithm, the PI may thus be used in effect to replace the health care provider and his decision making approach.

According to some embodiments, the algorithms used to create or be used within the mathematical model for the index may include, for example, a fuzzy logic inference that may be built, composed or enhanced using the health care providers knowledge and interpretation on the anticipated index value. For example, the index PI values may be given for any number and/or any combination of various types of medical parameters. According to some exemplary embodiments, the parameters used may include, for example, parameters, such as: $EtCO_2$, Respiratory Rate (RR), Heart Rate (HR), $SpO_2$, blood pressure, spirometry, relative flow parameters, $CO_2$ waveform patterns, blood gas, and the like.

According to additional exemplary embodiments, in order to determine the PI value based on, for example, four parameters (EtCO2, RR, HR and SpO2), a questionnaire and/or real patient log files may be sent to various health care providers (such as, nurses, respiratory therapists, physicians and anesthesiologists). The questionnaire may include a set of various cases with different parameter values. The health care providers may then be asked to assign a PI value according to a predefined code. For example, the predefined code may implicate that an index value of 10 implies a perfectly healthy normal condition. For example, the predefined code may implicate that an index value of 8-9 implies a normal condition. For example, the predefined code may implicate that an index value of 7 implies an understandable condition, which requires, however, more attention. For example, the predefined code may implicate that an index value of 5-6 implies that it is recommended to pay more attention. For example, the predefined code may implicate that an index value of 3-5 implies that it requires more attention and intervention is recommended. For example, the predefined code may implicate that an index value of 1-3 implies that intervention is required. In example 2 below, there is shown the predefined PI value code table used to determine the PI value. In addition, various clinical tests may be performed wherein the health care providers/experts are asked periodically to enter (in a blind or non-blind fashion) a PI value, that may be used afterwards for validation and fine-tuning of the algorithms' decision making.

According to additional embodiments, the fuzzy logic inference may be built using the consensus of the health care providers' data, such as may be obtained as explained above. For example, membership functions may be assigned for each parameter that is chosen to create the index, and the ranges for the various parameters may be determined For example, the ranges may include descriptions, such as, Normal, High, Very-High, Low and Very-Low. The index itself may thus have a number of membership functions that is determined by the scale of the values of the index. For example, an index, which is in the scale of 1 to 10, may have ten membership functions, one for each index value. Upon obtaining the membership functions, a rule set may be determined to relate the inputs (of the measured patient parameters) to the outputs, using the verbal descriptor of the membership functions, and consequently to determine the value of the index. For example, for an index that is determined by, for example, 5 parameters, if one parameter is "Very High" and an additional parameter is "High" and another parameter is "Normal" and an additional parameter is "Low" and another parameter is "Normal", then the Index value is X. The fuzzy logic operators used may include, for example, minimum for AND, maximum for OR, maximum for Aggregation and centeroid (center of gravity) of area for de-fuzzification. In example 2 hereinbelow, there are demonstrated exemplary fuzzy logic membership functions and an exemplary fuzzy logic rules matrix.

According to additional embodiments, the design of the fuzzy inference of the index model that is based on several health care providers' know-how may be further enhanced or fine-tuned by comparing to the average, or any other statistical results such as median or mode, index values determined by the health care providers. The fuzzy logic interface of the index model may further be validated. For example, validating the fuzzy inference model may be performed by an additional questionnaire or on real data, including sample cases. In the additional questionnaire, the Index values determined/calculated by the fuzzy inference model is shown, and the health care provider may opine on the values. By considering the opinion of the health care providers, fine-tuning of the fuzzy logic model may further be performed.

Additional information regarding fuzzy logic may be found, for example at: "Tutorial on Fuzzy logic", by Jan Jantzen, 1998, http://fuzzy.iau.dtu.dk/download/logic.pdf, the content of which is incorporated herein by reference in its entirety; "Fuzzy logic for just plain folks", chapters 1-3, that may be found at http://www.fuzzy-logic.com/Ch1.htm, http://www.fuzzy-logic.com/Ch2.htm, http://www.fuzzy-logic.com/Ch3.htm, the contents of which are incorporated herein by reference in their entirety; "A touch of gray" by Tran T. and Zomorodi, Z., that may be found at http://www.duke.edu/vertices/win94/fuzlogic.html, the content of which is incorporated herein by reference in its entirety.

According to some embodiments, when determining the ranges of the parameters that are used for the calculation of the index, several considerations should be taken into account, such as, for non-limiting examples, the age of the patient, weight of the patient, gender of the patient, current and/or prior medical condition of the patient, medications (currently and/or previously administered), known respiratory or cardiac disorders, pacemaker or other implant(s) in the patient, transplanted organs, and the like. Those considerations may be important for anintegrated pulmonary index, since various parameters may have different ranges for different patients. For example, it is known that there are differences in the normal ranges of HR and RR between adults and children at different ages, and hence, the PI values for the same parameters may differ for different classes of patients. Thus, PI-models may be designed for distinct ages, to account for the changes in the ranges of normal respiration rate and heart rate at different ages. Moreover, at ages lower than 1 year, the parameters value depends also on the child's weight. Therefore, various modes of operation may be used when determining a PI index, wherein the modes of operation takes into consideration additional parameters (factors) which may include specific characteristics of the patients, such as, for example, age, weight, gender, medical condition, medication, and the like, or any combination thereof. For example, with regards to age, several groups may be determined, each with its particular normal ranges of various parameters, such as HR and RR. For example, for a newborn (age of up to one month), normal RR may be in the range of, for example, about 30 to 60 BPM and the normal HR may be in the range of, for example, about 100 to 160 beats per minute. For example, for an infant (age of one month to one year), normal RR may be in the range of, for example, about 30 to 40 BPM and the normal HR may be in the range of, for example, about 90 to 150 beats per minute. For example, for a child (age of one to two years), normal RR may be in the range of, for example, about 22 to 30 BPM and the normal HR may be in the range of, for example, about 80 to 125 beats per minute. For example, for a child (age of 3 to 5 years), normal RR may be in the range of, for example, about 20 to 24 BPM and the normal HR may be in the range of, for example, about 70 to 115 beats per minute. For example, for a child (age of 6 to 12 years), normal RR may be in the range of, for example, about 16 to 22 BPM and the normal HR may be in the range of, for example, about 60 to 100 beats per minute. For example, for a child (age of 1 to 2 years), normal RR may be in the range of, for example, about 22 to 30 BPM and the normal HR may be in the range of, for example, about 70 to 125 beats per minute. For example, for a child (age of 3 to 5 years), normal RR may be in the range of, for example, about 19 to 25 BPM and the normal HR may be in the range of, for example, about 70 to 110 beats per minute. For example, for a child (age of 6 to 1 year), normal RR may be in the range of, for example, about 14 to 24 BPM and the normal HR may be in the range of, for example, about 70 to 110 beats per minute. For example, for an adult (age over 12 years), normal RR may be in the range of, for example, about 10 to 18 BPM and the normal HR may be in the range of, for example, about 60 to 100 beats per minute. Changes to the fuzzy logic interface model used to determine the index may apply to the membership functions of the parameters whose ranges are influenced by the specific patients parameters. For example, for the age influence on the PI index, the changes to the fuzzy logic model may be in the ranges of the RR and HR membership functions, as further illustrated in FIG. 2, described below.

According to some embodiments, the calculations of the index may use averaged input values, in order to prevent noise. The averaging time window may be constant (such as, of example, 30 sec for adult mode, 15 sec for pediatric modes). In addition, or alternatively, the averaging time window may be a non-constant and/or adaptive time window that be determined by various algorithms.

According to other embodiments, several special cases may arise during monitoring that may require specific attention. Such cases may include, for example, a condition wherein no breath is detected (Apnea); an Auto Zero condition; a measuring probe is not connected, and hence the measured parameter is not recorded. In the following cases the monitoring device may present a PI value: Apnea—once No-breath is detected (more than Xsec with no new detection of $CO_2$, X is defined by the user, usually 20-30 sec), $EtCO_2$=0, RR=0. These values are valid, and the PI is expected to slowly decrease. Once breathing resumes, $EtCO_2$>0 after one breath, RR>0 after 2 breaths, PI is handled the same way, that is, it is expected to slowly increase. Auto Zero—PI may present the last value. When a measuring probe is disconnected, the averaging may be carried out using the available measurements, disregarding the not-valid measurements. Only after the time window for averaging passes, would there be a non-valid input and hence the PI would be not-valid as well.

According to some embodiments, when determining the value of the index, for example, by using a fuzzy logic interface, non-linear, or any form of interaction between various measured/sensed parameters may be taken into consideration when calculating the index value. Such interaction between the parameters may include, for example, synergistic effects between various parameters. At some cases, a combination of parameters may have a synergetic effect, and by using fuzzy logic rules, the non-linear interactions between parameters is evident, and thus the synergy between the input parameters used for calculation of the index may be captured. For example, an example of a synergetic effect of the rules of the fuzzy logic interface used to determine a PI value: Higher than normal RR level alone could be perceived as a risk, however, when it is accompanied by a higher than normal level of $ETCO_2$, the risk level is lower, as this is the expected normal physiological response. Several health related parameters may be used in the calculations. For example, as illustrated in example 2 hereinbelow, If ($EtCO_2$ is Very High) and (RR is Very High) and ($SpO_2$ is Normal) and (HR is High) then (PI is 2)). Such calculation takes into consideration the various membership functions and synergistic effects between various parameters. In this example, when $EtCO_2$ is very high and RR is very high, the PI=3, however, while $SpO_2$ is normal and hence it would not affect the PI value, the HR is High, which leads to a reduction of one level in the PI value, which becomes 2. In a different example, if $EtCO_2$ is high and RR is normal and $SpO_2$ is low and HR is normal, then PI=6. In this example, when $EtCO_2$ is high and RR is normal then PI=7, however, since $SpO_2$ is low, it leads to a reduction of 1 in the PI. Since HR is normal, it does not further affect the PI, and hence the PI=6.

According to some embodiments, the fuzzy logic interface may further be adjusted for noise and artifacts filtering, wherein noise and artifacts are events that are identified visually and/or by other identification means, which are not identified as authentic medical conditions. For example, the inputs to the fuzzy logic (interface) module may be averaged over a moving time window using a constant window length (such as, for example, 30 sec for adult mode, 15 sec for pediatric mode) or an adaptive window length. The adaptive window length may be pre-defined, for example, by the variability of the inputs at the most recent measurements, as may be determined, for example, by various algorithms; or alternatively, may be dynamically adjusted, as by expanding or contracting the time window in response to values of criteria. For example, the inputs to the fuzzy logic may be filtered out from averaging and further calculations as a result of identification of artifacts. The artifacts' identification may be based, for example, upon $CO_2$ waveform analysis. For example, when a waveform is classified as an artifact (for example, when a patient is eating, talking, and the like), the $EtCO_2$ and RR related to that time period may be updated using a modified mathematical algorithm for averaging. Alternatively, that time period may be ignored. For example, when a patient is receiving oxygen supply, the oxygen supply may result in dilution of the $CO_2$ signal. Correction for such dilution artifact may be done, for example, for the $EtCO_2$ level.

According to further embodiments, the change in the PI value over time (PI trend) may be displayed graphically. The graphic display may exhibit the PI trended over the last "n" (time units) of monitoring. For example, n may be any time period in the range of 5 minutes to 12 hours. This display may be used to indicate the patient's status, such as, for example: stable, improving, deteriorating, as well as providing a depiction of the rate and change of the patient's status. Displaying of the PI trend may simplify the assessment of the changes in the ventilatory condition of the patient as compared to assessing the patient condition based on the trend of the individual parameters When looking at the trends of the individual parameters, it may not be easy and intuitive to determine the patients status and change in status, without taking into consideration the absolute values of the individual parameters and their interactions, since both an increase or decrease in any of those parameters may be "good" (improvement) or "bad" (deterioration), depending on the absolute value of the parameter. For example, a decrease from a higher than normal absolute value towards the normal absolute value may be considered "good", while a decrease from a normal value to a lower than normal value may be considered "bad". Likewise, an increase from a lower than normal value towards the normal value may be considered "good", while an increase from a normal value to a higher than normal value may be considered "bad". The PI trend may be depicted as a graphic display of the PI values over time. The duration period of the trend may be chosen to be over any time period in the range of, for example, between 5 minutes to 12 hours of the last measurements. The resolution of the graphical display may change accordingly in correlation to the selected time period. By providing a trend of the PI index an estimation of how the patient's respiratory status is changing over time, such as, stable, improving or deteriorating may be obtained. This may be attributed to the fact that the PI itself is an overall picture of the patient's respiratory status, and the changes in value of this index may provide a clear picture as to whether the patient condition is changing or not.

According to additional embodiments, the trends of the parameters (that is, the change of the values of the parameters over time) may also be taken into consideration when determining the index and may further be displayed.

According to further embodiments, an index of reliability may also be determined. The index of reliability (referred to herein also as "reliability index" or "RI") may provide a measure of the reliability of the data and more specifically, the reliability of the PI. For example, the reliability index may be used to predict and anticipate artifacts. The reliability index may be determined, for example, by analysis of the $CO_2$ waveforms, as depicted by a capnogram. If breath flow is also measured, its waveforms may also be used for this purpose. The use of breath flow measurements may refine and improve the index of reliability. Breath flow waveforms strongly complement the waveforms created by the $CO_2$ measurement, since both measurements represent essentially the same event, which is the breath cycle. While the breath flow relates to the envelope of the waveform, the $CO_2$ relates to the $CO_2$ concentration within the envelope. Using both parameters may reveal and uncover and assist in distinguishing between a valid measurement, a noise, an artifact, and the like. The reliability index may assist the user (the health care provider) to decide if a low PI value or any of the other measured values is real (and represent a genuine clinical event), transient or an artifact. The reliability index may further assist the health care provider in assessing how much credibility may be attribute to the displayed PI value. In addition, the reliability index may allow the health care provider to detect artifacts, such as when the monitoring device is not placed properly on the patient, the monitoring device is not measuring properly, and the like. The reliability index may be determined from both analysis of the $CO_2$ waveform and respiration rate pattern. By obtaining data from controlled studies, the characteristic patterns attributed to artifacts may be defined. Analysis of the real time waveform depicted by the monitoring device and comparison to the known artifact patterns may be used to calculate the reliability index.

According to yet further embodiments, confidence (reliability) level may accompany the index value. The confidence (reliability) level may further be displayed for the health care provider. The confidence (reliability) value may be a number in the range of, for example 0 to 1. The confidence (reliability) level value may be determined/calculated from the standard deviation (std) of the various input variables (measured/sensed) parameters, as well as artifacts, if such are identified. Furthermore, the various input variables may be weighted according to their confidence (reliability) level. Other mathematical, including statistical, methods of calculating or determining confidence intervals levels or other interval estimates may be used as will be understood by one of skill in the art.

According to additional embodiments, a pause frequency parameter may be determined. This parameter may include a measure of events wherein no breathing is detected over a period of time. The events of lack of breathing may include, for example, pause and apnea events; and the pause frequency parameter may include a measurement of the patient's pause and apnea events over a period of time. Very often patients may stop breathing for short periods of time either because of mechanical obstructions or sometimes because of a central (brain) block. The pauses (apnea events) are periodic and their frequency may be indicative of the condition of the patient. The pause frequency parameter may be determined/calculated from the $CO_2$ waveform, as obtained by the capnogram. A pause event may be defined, for example, as any inhalation stage that persists for longer than any number of seconds in the range of, for example, 5 to 40 seconds (such as for example 20 seconds), and proceeds after an exhalation period lasting less than any number of seconds in the range of, for example, 5 to 20 seconds (such as, for example, 10 seconds). The time periods may be determined, for example, according to the average time of the last three exhalation cycles. Such determination of a pause event may be used to exclude a slow, rhythmic breathing pattern from being defined as a group of pause events. In addition, a maximum time out of, for example, 100 seconds may be determined. If a pause is detected, a new pause can only be counted if at least three new, valid breath cycles were detected beforehand. Thus, the pause frequency parameter may be defined by the number of pause events per period of time (such as, for example, an hour). The pause frequency may be updated at any time interval, such as for example, every 5 minutes, after the period of 1 hour. The values of the pause frequency may further be stored and used for the display of the pause frequency trend, wherein the trend data represent the change of the pause frequency over time. According to some exemplary embodiments, during the first hour (when insufficient data has accumulated), a value may be provided and updated, for example, every 15 minutes until 1 hour has been reached (wherein during this time period the frequency is determined/calculated as if it was determined/calculated for 1 hour). During this time period an indication showing that the pause frequency is still based on a shorter period than 1 hour may be displayed. Since the health care provider, such as a nurse, may not be constantly present next to the patient and/or the monitoring device, and may not constantly track (monitor) the patient condition, a parameter, such as the pause frequency parameter, which is a periodic type effect may not easily be observed by the health care provider if not otherwise tracked by the monitoring device. In addition, according to further embodiments, the pause amplitude parameter may also be determined. The pause amplitude parameter may include the time length (such as, for example, in the range of 5 to 60 seconds) of each of the detected pause events and the dispersion of the time length of those pause events over a period of time (such as, for example, over a time period of 60 minutes).

According to some embodiments, various additional parameters (factors), in addition to the main parameters according to which the index is determined, may be added for the calculations of determining the index. The additional parameters (factors) may include various patient specific parameters that may be characteristic of the patient. The additional parameters (factors) may include "on-line" parameters that are health related parameters that may be sensed/measured on-line, in real-time, and/or may include other input(s) (such as, for example, by a keyboard, switches or touch panel) or other parameters (such as, for example, age, gender, weight, and the like). The additional parameters may include "off-line" parameters that may include parameters that are related to the patient's medical history and demographic and/or parameters that relate to a recent/current health condition of the patient. In addition, the trends of the additional parameters (that is, the change of the values of the parameters over time) may also be taken into consideration when determining the index. Using additional parameters for calculation of the index may be dynamic, that is, according to necessity or variability or of averaging weight(s), at any given time. The additional parameters may be added either manually or by any route of communication. For example, with respect to a PI index that is determined by the parameters of HR, RR, $EtCO_2$ and $SpO_2$, additional on-line parameters may include such parameters as, but not limited to: $CO_2$ wave form and $CO_2$ wave form related parameters, such as, for example, changes in $ETCO_2$, a slope of the increase in the $CO_2$ concentration, a change in a slope of the increase in the $CO_2$ concentration, time to rise to a predetermined percentage of a maximum value of $CO_2$ concentration, an angle of rise to a predetermined percentage of a maximum value of $CO_2$ concentration, breath to breath correlation, CAP-FEV1 (forced expiratory volume over 1 sec obtained from at least one capnographic measurement, a measure of flow), CAP-FEV1/FVC, inhalation to exhalation ratio (for example, the inhalation to exhalation ratio, multiplied by the $EtCO_2$ measured values, may be used to determine how much $CO_2$ is being ventilated), duty cycle of the $CO_2$ (which is related to measure of minute ventilation), and the like; breathing related parameters; heart function related parameters, such as, for example, blood pressure, NI blood pressure, systolic to diastolic ratio, and the like; neurological parameters; systemic perfusion related parameters; visual parameters; flow rate; spirometry; and the like, or any combination thereof. For example, additional off line parameters may include such parameters as, but not limited to: parameters that are related to a patient's history and demographic such as, for example, age, gender, weight, current diagnosis, medical history (for example: smoking, heart disease, lung disease, sleep apnea, medications taken, pace maker) and the like, and any combination thereof. Additional off line parameters that are related to a recent health condition of the patient may include such parameters as, but not limited to: medical treatments (for example medications given, ventilation, oxygen supply), lab tests (for example, blood gases, pH, general blood tests, urine tests), whether the patient is intubated or not, whether the patient is asleep (during sleep, stable $CO_2$ waveforms are expected, non-stable waveforms are indicative of poor condition, while in an awake patient the opposite is expected, that is, non-stable waveform are normal, while stable wave forms may be indicative of a poor condition); and the like, or any combination thereof.

Figure 2:
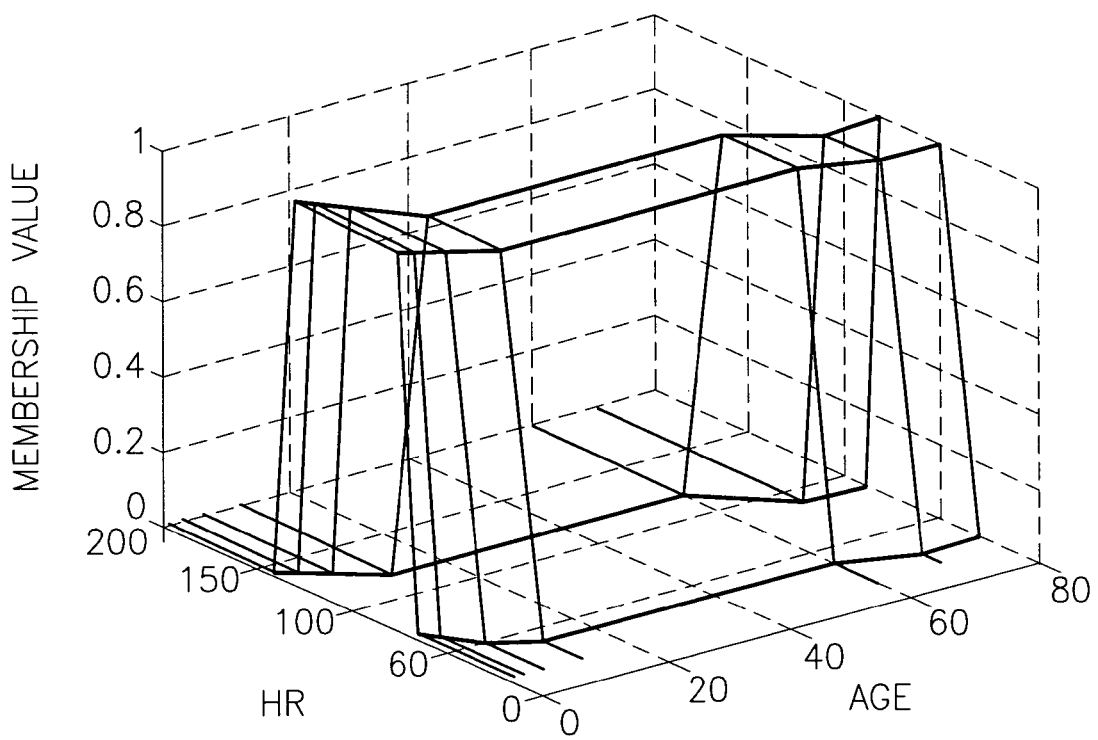
FIG. 2—An exemplary graph depicting membership as a function of age, when using a fuzzy logic interface model, according to some embodiments.

According to some embodiments, the additional parameters (factors) may be used to manipulate the inputs to the membership functions, for example, by changing the limit ranges of various measured patient parameters. For example, evaluation of Heart Rate (HR) ranges of normal, high and low may further depend on the patient's age. Accordingly, the parameters of the membership functions may be defined as a linear or non-linear function of age. Reference is now made to FIG. 2, which illustrates an exemplary value of membership function as a function of age. The graphs shown in FIG. 2 represent the value of the membership function (mf) of the heart rate (HR, beat/pulse per minute (bpm)) as a function of Age (years). As shown in FIG. 2, the membership function generates a trapeze shape, when using 4 parameters. When the parameters depend on age, different shape may be generated, according to the age. For example, at the age of 1 year old, the range of normal heart rate is at higher bpm than the range for normal heart rate for the ages 12-60 years old (the parameters for age 1 are: 70 80 135 145 bpm, and for ages 12-60: 40 60 100 120 bpm). Following the parameters that define the boundaries of the trapezes (bold lines) and the trapezes (thin lines) illustrates the dependency of the membership function on age and HR. (In the graph, The X-axis is age in years; the Y-axis is Heart rate in bpm; and the Z-axis is the membership function value for Normal HR in a scale 0-1.

According to further embodiments, the additional parameters (factors) may be used for the creation of additional rules that may be implemented with, for example, the fuzzy logic interface model. The additional parameters may be used as any of the basic (primary) parameters, using their membership functions and incorporation in their rules, such as exemplified in FIG. 4A, belowherein. The additional rules may be in a flat or hierarchical structure. For example, an additional on-line parameter that may be used for the calculation of a PI index may include a parameter such as, for example, the diastolic blood pressure (BP), that may be used in conjunction with HR as shown, for example in the following rules: If HR is High and BP is High then PI=PI (normal HR)−2; If HR is High or Low and BP is Normal PI=PI (normal HR)−1; and the like.

Figure 3:
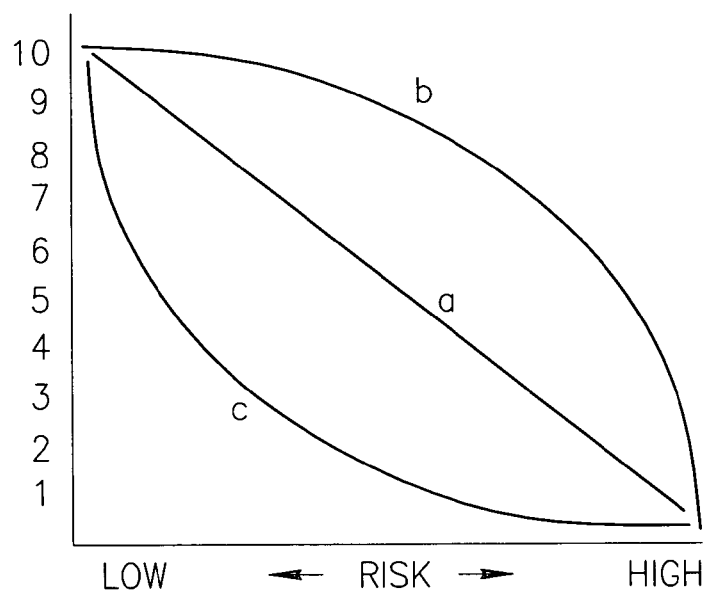
FIG. 3—An exemplary graph depicting the PI value as a function of the level of risk.

According to further embodiments, the additional parameters (factors) may be used for the creation of an adaptive index risk function. The value of the index reflects the risk to a patient's health. The risk association with a specific index value may differ at different conditions. Such different conditions may allow the use of additional parameters such as, for example, the patient's illness, the hospitalization department, and the use of such additional parameters may be used to revise the risk association function. For example, with respect to the PI index, the value of the index reflects the risk to a patient's health, such that, for example a PI index value of PI=[8-10] means that the patient is in a good condition. The risk association with a specific index value may differ at different conditions. Thus, a linear PI-Risk function may be altered to reflect higher sensitivity for changes at low PI values, or at high PI values. The PI may be determined/calculated as is, and its final value may be changed according to the association functions. Such risk association function is illustrated, for example, in FIG. 3, which illustrates graphs depicting the PI value (on a scale of 1 to 10, Y-Axis) with relation to the level of risk (from low to high, x-axis). Line a in the graph illustrates a linear PI-Risk function; line b illustrates a graph which reflect higher sensitivity for changes at low PI values; line c illustrates a graph which reflect higher sensitivity for changes at high PI values. In this example, PI, which equals to 5 in line a, may turn to 2 using line c association rule.

Figure 4A:
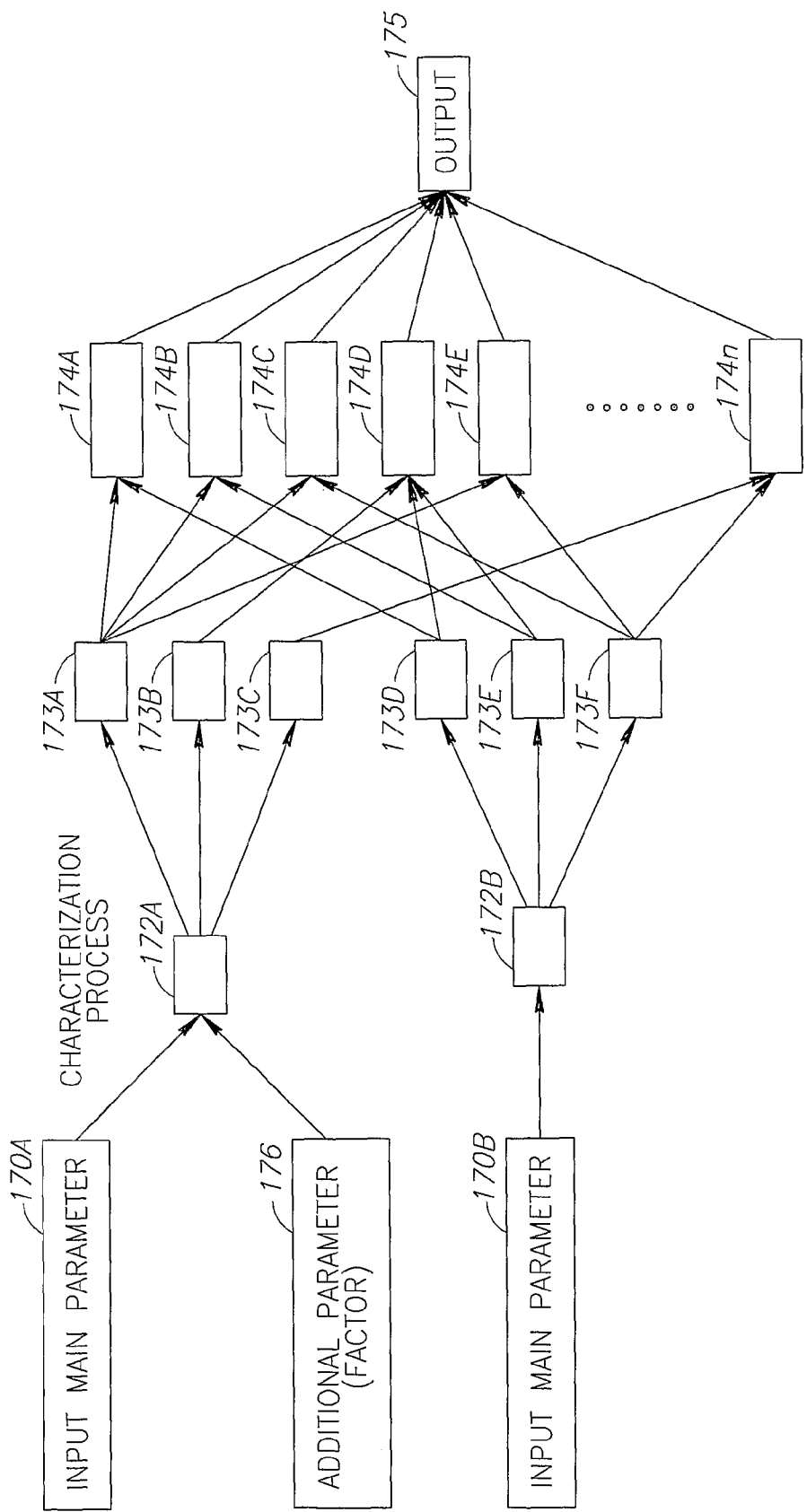
FIG. 4A—An exemplary illustration of a method of calculating an index value, according to some embodiments.

Reference is now made to FIG. 4A, which illustrates an exemplary block diagram scheme of a method of calculating a PI index using a fuzzy logic interface, according to some embodiments. As shown in FIG. 4A, input main parameter, such as parameter 170A, enters a characterization process (such as process 172A). The input parameters may include any number of sensed/measured/determined patient parameter that may be directly or indirectly sensed/measured/determined. The input parameters may include any plurality of sensed/measured/determined patient parameters. For example, the input main parameter may include such parameters as, but not limited to: heart rate, respiration rate, $CO_2$ related parameters, $O_2$ related parameters, electrocardiogram (ECG), encephalogram (EEG), blood pressure, spirometry, and the like, or any combination thereof. In the characterization process, the respective membership value to each characteristic group (such as groups 173A-C) is calculated/computed/assigned. The characteristic groups may be labeled, for example, as: "Normal", "High", "Low", "Very High", "Very Low", and the like. The same process may be applied onto any number of input main parameters, such as, for example, input parameter 170B, which may be characterized by characterization process 172B, where the respective membership value to each characteristic group (such as groups 173D-F) is calculated. At the next step, various combinations of pairs of each group enter an Output Characteristic Group (such as, for example, output characteristic groups 174A-n, wherein n may include any integer number higher than 0). For example, as shown in FIG. 4A, characteristic groups 173A and 173D may enter Output Characteristic Group 174A. The membership values of both parameters groups, the weights related to each and a logic operator combining them (such as, for example, "AND", "OR") may be used to calculate/determine/compute/assign the membership value for each Output Characteristic Group. The topology of the network is designed, for example, using medical experts' knowledge, clinical trials, literature, sample cases, and the like. Eventually, an output value (such as output value 175) is calculated from all values of membership functions, for example, by an aggregation function (such as, for example, MAX, and the like) and/or by an averaging function (such as, for example, centeroid, mean, average, and the like). According to additional embodiments, the method of calculating an index may further include the use of various additional parameters (factors), in addition to the main parameters. The additional parameters (factors) may include various patient specific parameters that may be characteristic of the patient, such as, for example, blood pressure, age, medical condition, sedation, patient awake, patient asleep, and the like. For example, an additional parameter (factor), such as, for example, additional parameter (factor) 176 may enter into one or more of the characterization processes and may thus control/tune the membership functions and membership value for each Output Characteristic Group that result from the characterization process.

Figure 4B:
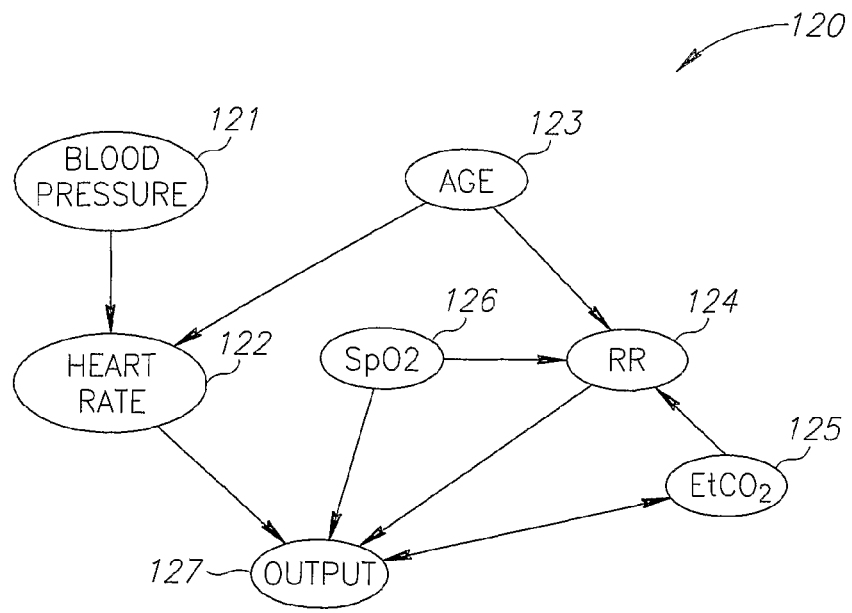
FIG. 4B—An exemplary illustration of a Bayesian network for calculating an index value, according to some embodiments.

According to additional embodiments, the calculation model may include a Bayesian network. A Bayesian network, as known in the art, may include a graphical representation of relationships between variables based on probability theory. A Bayesian network includes a directed a-cyclic graph with nodes representing variables that are associated with a table of conditional probabilities. Nodes are connected by arcs, which model the relationships between variables. The probability of a node can be calculated when the values of other variables are known. A Bayesian network has a learning capability using known cases and it may tolerate missing data. Topology and probabilities of a Bayesian network may be assigned using, for example, experts' knowledge, textbooks, clinical trials, sample cases, and the like. Bayesian network nodes may include various parameters and/or inputs and/or factors, that may include, for example: measured/sensed parameters (such as, for example, $EtCO_2$, RR, $SpO_2$, HR, blood pressure, and the like); medical condition (such as, for example, heart failure, asthma, smoking, lung disease, and the like); demographics (such as, for example, age, gender, weight, and the like); lab test results (such as, for example, blood gases, pH, urine tests, and the like); medications (such as, for example, steroids, sedatives, anti-inflammatory drugs, and the like); and the like. The node may have discrete or continuous values. Considering the various parameters and/or inputs, a Bayesian network may be used to compute/evaluate/determine a health related index, such as, for example, a PI that represent the probabilities of the status of the patient. The Bayesian network may further be used to compute/evaluate/determine the probabilities of a diagnosis (such as, for example, hyperventilation, hypoventilation) and may further provide recommendation for additional tests and/or interventions. Additional information regarding a Bayesian network may be found, for example at: "A Tutorial on Learning with Bayesian Networks" by Heckerman D, in "Learning in Graphical Models" by M. Jordan, ed. MIT Press, Cambridge, Mass., 1999, the content of which is incorporated herein by reference in its entirety; "Bayesian Networks" by Ben-Gal in F. Ruggeri, R. Kenett, and F. Faltin (editors), Encyclopedia of Statistics in Quality and Reliability, John Wiley & Sons (2007), the content of which is incorporated herein by reference in its entirety. Reference is now made to FIG. 4B, which illustrates an exemplary Bayesian network topography, according to some embodiments. As shown in FIG. 4B, exemplary Bayesian network 120, may illustrate relationships (represented by arrows) between various parameters and/or factors and/or inputs, such as, for example, Blood Pressure (121), Age (123), Heart rate (122) $SpO_2$ (126), Respiration Rate (124), $EtCO_2$ (125). By assigning the various relationships between the various factors an output (127), such as an index, (such as PI) may be determined/calculated/computed.

Figure 4C:
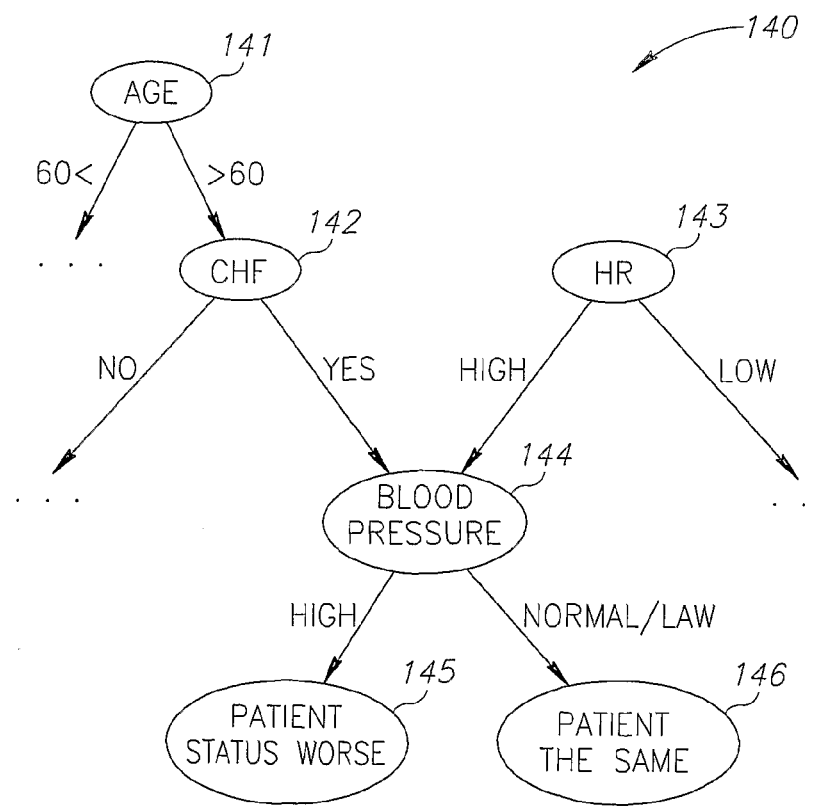
FIG. 4C—An exemplary illustration of a decision tree graph structure for calculating an index value, according to some embodiments.

According to additional embodiments, the calculation model may include a decision tree. A decision tree is a predictive model that may be used to map observations regarding an item to conclusions regarding the item's target value. The tree has a hierarchical graph structure consisting of nodes and directed edges. The top layer may include input nodes (such as, for example, parameters and/or inputs/and/or factors, such as, but not limited to: measured/sensed parameters (such as, for example, $EtCO_2$, RR, $SpO_2$, HR, blood pressure, and the like); medical condition (such as, for example, heart failure, asthma, smoking, lung disease, and the like); demographics (such as, for example, age, gender, weight, and the like); lab test results (such as, for example, blood gases, pH, urine tests, and the like); medications (such as, for example, steroids, sedatives, anti-inflammatory drugs, and the like); and the like). Decision nodes determine the order of progression through the graph. The "leaves" of the tree are all possible outcomes or classifications, while the "root" is the final outcome, that may include, for example, the patient status classification, recommendations for intervention, and the like. The tree may be built using experts' knowledge, sample cases, literature, clinical trials, and the like. Methods for building decision tree may include, for example, algorithms, such as, C5.0, CART and ID3 which are decision tree algorithms well known in the art. There may be reinforcement learning to refine the tree structure and parameters. The outputs classification may be assigned with corresponding probabilities. An ensemble of trees may be generated to incorporate different trees, to produce a more complex classification. Additional information regarding decision trees may be found, for example at: "Improved Use of Continuous Attributes in C4.5", by J. R. Quinlan, Journal of Artificial Intelligence Research, 4:77-90, 1996, the content of which is incorporated herein by reference in its entirety. Reference is now made to FIG. 4C, which illustrates an exemplary decision tree graph structure, according to some embodiments. As shown in FIG. 4C, exemplary decision tree graph structure 140 may illustrate directed edges and nodes (represented by circles and arrows), which relate between various parameters and/or factors and/or inputs, such as, for example, age, Coronary heart disease (CHF), heart rate (HR), blood pressure and their predicted outcome. The nodes may include input nodes and/or decision nodes, which may be used to determine the order of progression through the decision tree graph. For example, as illustrated in FIG. 4C, input node 141 (age) may lead to two decision nodes, represented by arrows, for example, age is below 60 or above 60. According to each of the decision nodes, progression to other input nodes is determined. For example, as shown in FIG. 4C, if age is above 60, CHF input node (142) is considered. If the CHF input node is positive, then another input node, such as, for example, blood pressure (144) is considered. In addition or alternatively, in parallel or in series, other input nodes may be considered. As shown in FIG. 4C, Heart rate (HR) input node (143) may be also considered in parallel. If the HR is high, then the blood pressure input mode (144) is also considered. Additional decisions nodes are represented by tripled dots. The "root" of the tree represents the final outcome of the decision tree. For example, the outcome may include if the patient status (condition) is the same (such as, for example, outcome 146), or if the patient status (condition) is worse (such as, for example, outcome 145).

According to additional embodiments, the calculation model may include a feed forward neural network. A feed forward neural network is a biologically inspired classification algorithm. It may include simple neuron-like processing units, organized in layers. Every unit in a layer is connected with the units in the previous layer. The connections may not all be equal, as each connection may have a different strength or weight. The weights of the connections encode the knowledge of a network. Often the units in a neural network are also called nodes. Data enters the network at the inputs and passes through the network, layer by layer, until it arrives at the outputs. During normal operation, that is, when it acts as a classifier, there is no feedback between layers. During the learning phase, the weights in the network may be modified. All weights are modified in such a way that, when a pattern is presented, the output unit with the correct category will have the largest output value. Learning may be carried out using the back-propagation algorithm. Reinforcement learning is also possible. A hierarchical structure of networks may also be designed. The inputs to the network may include, for example, measured/sensed parameters (such as, for example, $EtCO_2$, RR, $SpO_2$, HR, blood pressure, and the like) and/or various additional parameters (factors) that are patient specific and may be characteristic of the patient, such as, for example, blood pressure, age, medical condition, sedation, patient awake, patient asleep, and the like. The output may include, for example, a health related index, such as, a PI that may represent the patient status classification. The network may also capture changes over time (trend) of the input parameters by adding input nodes of previous time points. Additional information regarding feed-forward neural networks may be found, for example at: "Pattern classification" (2nd edition), by Duda, R. O., Hart, P. E., Stork, D. G., (2001) Wiley Publishers, the content of which is incorporated herein by reference in its entirety; "Neural Networks for Pattern Recognition" by Bishop, C. M. (1995), Oxford University Press.

Figure 4D:
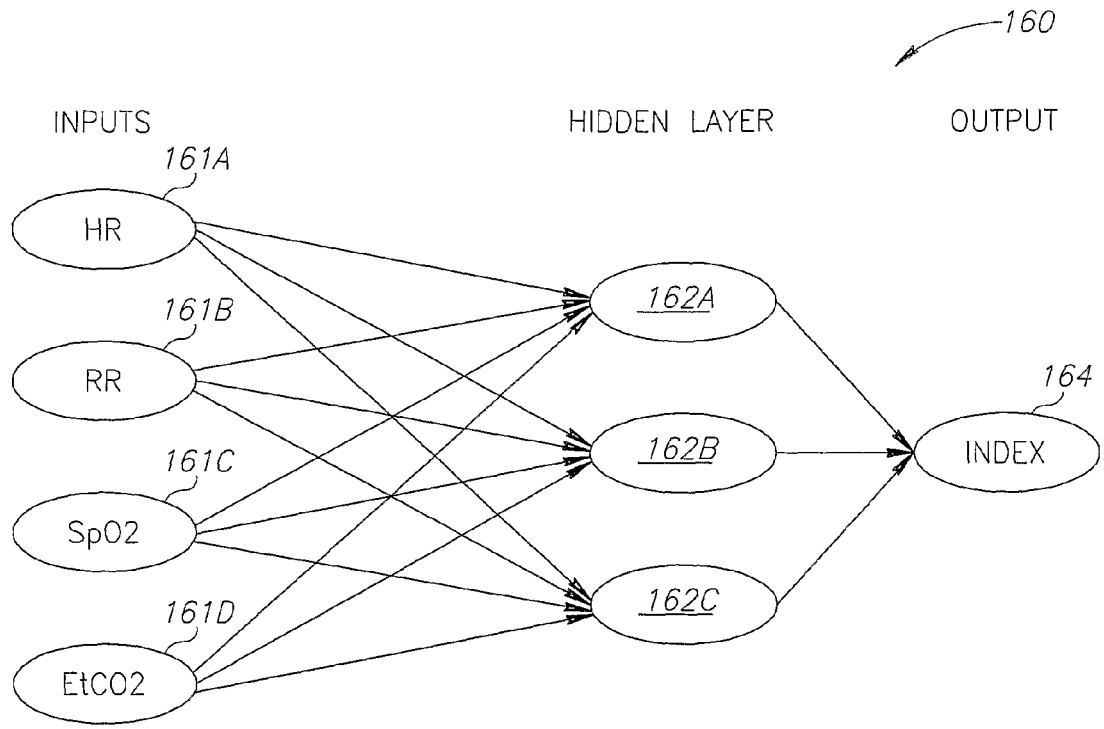
FIG. 4D—An exemplary illustration of a feed forwards neural network for calculating an index value, according to some embodiments.

Reference is now made to FIG. 4D, which illustrates an exemplary feed forward neural network, according to some embodiments. As shown in FIG. 4D, exemplary feed forward neural network 160, may illustrate propagation of information (represented by arrows) from various input measured/sensed parameters, such as, for example, Heart rate (HR, 161A), Respiration rate (RR, 161B), $SpO_2$ (161C), $EtCO_2$ (161D), to and through neuron-like processing units (layers) of the network (such as, for example, hidden layers 162A, 162B and 162C). From the information processed/evaluated/determined in the various layers of the network, an output (164 in FIG. 4D), such as, for example, PI, may be determined. The weights and relationships between the various layers may be modified, for example, by employing a feedback mechanism, which may be used, in particular, during a learning phase.

Figure 5:
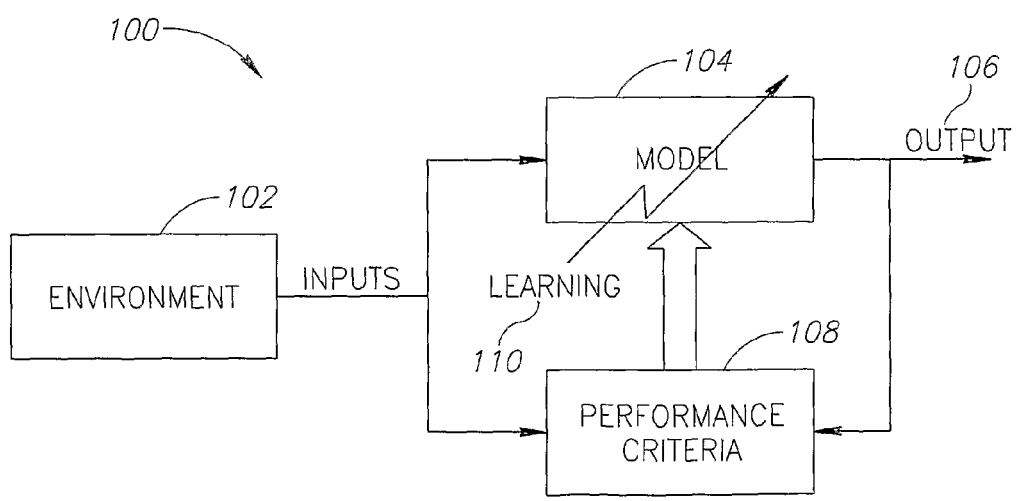
FIG. 5—An exemplary block diagram scheme of a learning model, according to some embodiments.
Figure 6A:
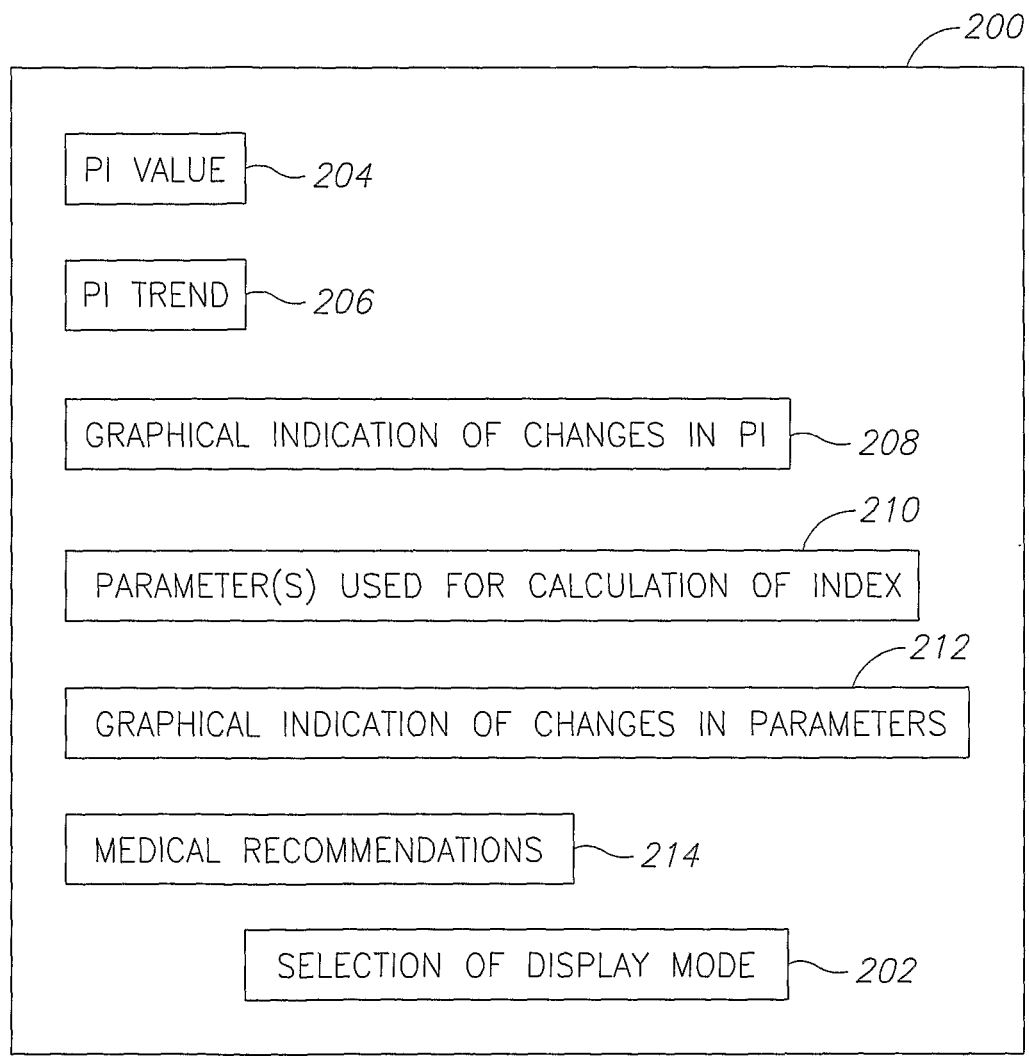
FIG. 6A—A block diagram illustration of graphical user interfaces, according to some embodiments.
Figure 6B:
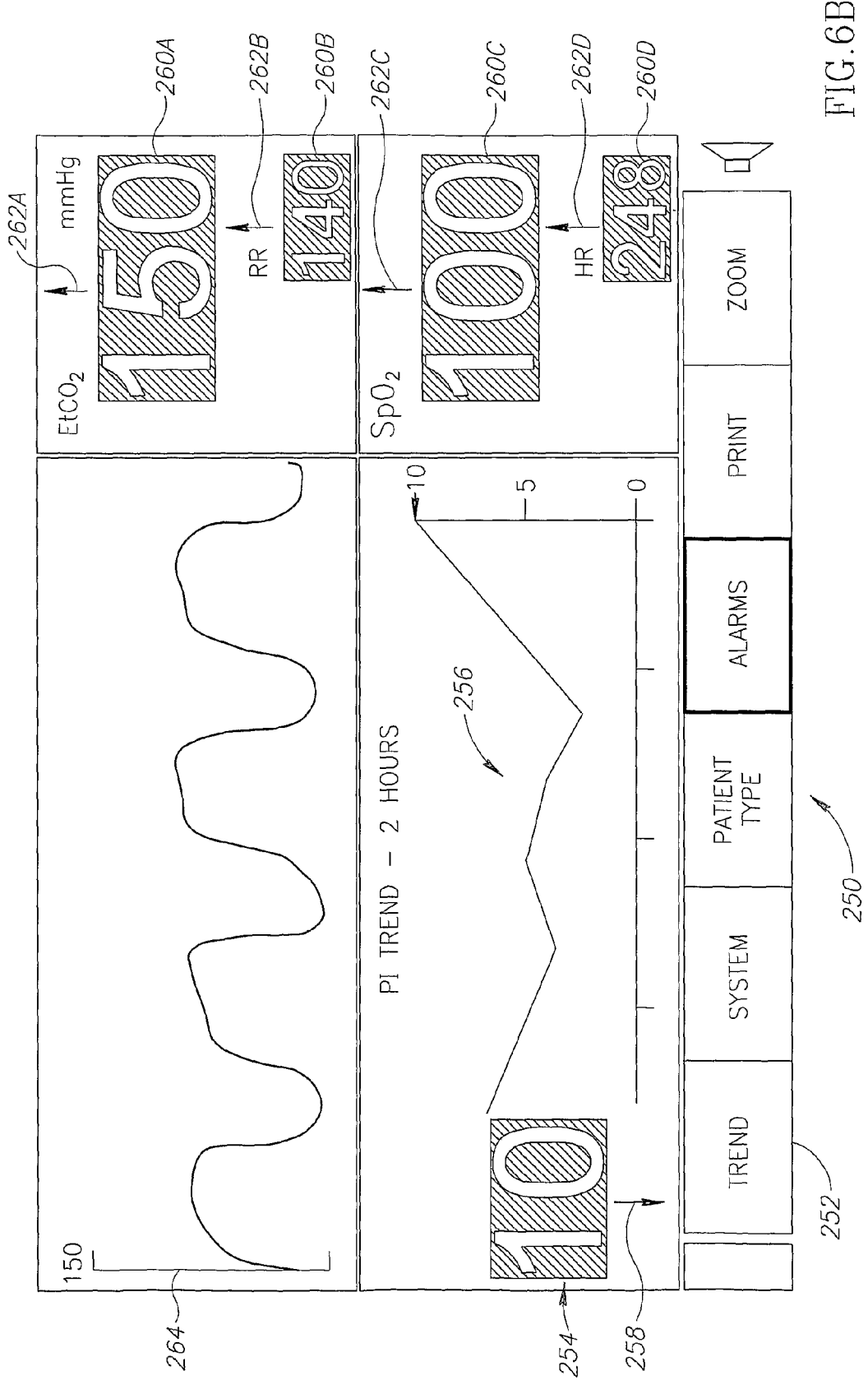
FIG. 6B-D—Exemplary illustrations of a graphical user interface, according to some embodiments.
Figure 6C:
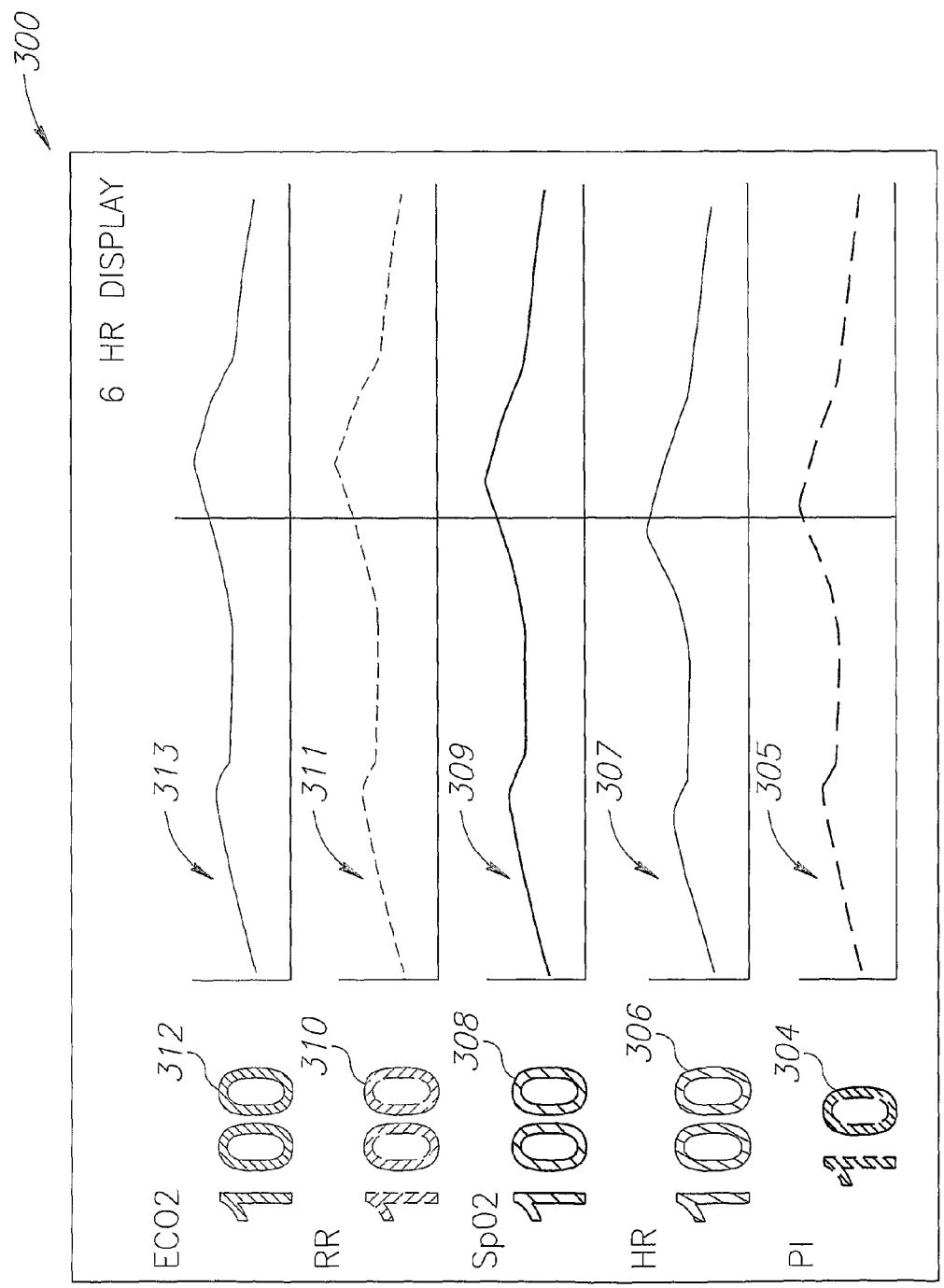
Figure 6D:
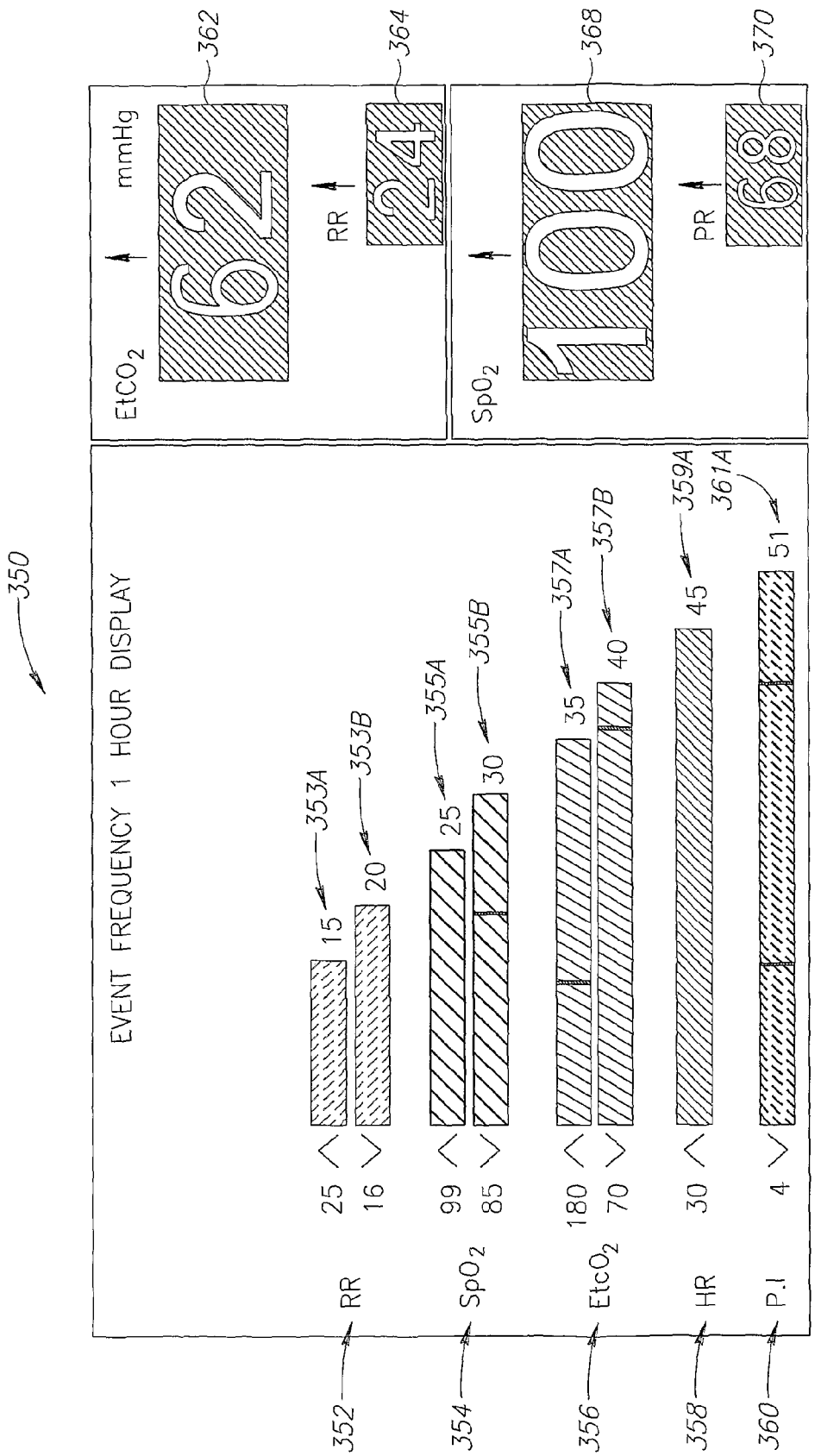

According to further embodiments, when determining the index value, a learning model may be used in order to define or refine the index risk association function, and/or to fine-tune rules and/or to fine-tune membership functions, according which the index is determined/calculated. As shown in the FIG. 5, a learning model scheme (100) may include three main blocks: 1. Environment (102), which sends measured patient parameters as inputs to the model. The parameters may include such parameters as, but not limited to: $ETCO_2$, $SpO_2$, RR, HR, and the like. 2. The calculation model (104) may include various mathematical models, such as, for example, but not limited to: Fuzzy inference model, Bayesian network, decision tree, neural networks, radial base functions, linear regression models, and non-linear regression models. For example, the calculation model may include a fuzzy inference model. The calculation model may then calculate an output (106) that may include, for example, the PI value. For example, the calculation model may include a Bayesian network. For example, the calculation model may include a decision tree. For example, the calculation model may include a feed forward neural network. 3. Performance criteria (108) may include a score that evaluates the reliability (quality) of the prediction of the model. The criteria may be estimated by, for example, a health care provider expert. In addition, or alternatively, the criteria may be an automatic estimation using additional data collected regarding patient status and medical interventions. Using the performance criteria, a learning process (110) may be applied in order to maximize the performance until convergence is attained. Learning and optimization may be carried out using various methods, such as, for example, but not limited to: neural networks, a support vector machine (SVM), genetic algorithms, simulated annealing and expectation-maximization (EM), and the like. Learning may be carried out off-line to gain a better general model, or on-line as an adaptation of the model to fit each specific/individual patient. In the last case, the longer the patient is monitored, the more over-fitting of the model towards his state.

According to some embodiments, the monitoring device may further include and display, medical recommendations to the health care professionals. The medical recommendations may be deduced from analysis of at least some of the individual parameter's values and patterns and comparison of the measured values and patterns to the known ranges and patterns of the individual parameters. These recommendations may be displayed, in addition to the indications derived from the determined/calculated condition-index-value. The medical recommendations may be based on, for example, the characteristics of the $CO_2$ waveforms (presented as a capnogram) and RI values. The recommendation provided to the health care provider may include, for example such recommendation as: If $CO_2$ waveforms are observed with characteristics indicative of a partial obstruction (such as long downward slope of the waveform), then the device may recommend "open airway" or "check airway". If the $CO_2$ waveforms are very low but exhibit an excellent form indicative of low blood flow to lungs, then the device monitor may recommend: "check blood pressure" or similar. The detection of known $CO_2$ waveform patterns, which are indicative of known patient conditions that should and could be treated to improve the patient care, may be used in triggering and issuing the recommendations to the health care professional. For example, it is very common that a patient entering partial obstruction promote a waveform pattern wherein the downward slope of the capnogram increases in time, with a gradual fall. In such an instance, a notification to the health care provider, such as "check patient airway" may be issued. For example, if the $CO_2$ waveforms pattern become very rounded and low, which is indicative of a mechanical problem with the cannula of the capnograph, a recommendation, such as, "check cannula interface" may be issued. Those and other similar medical recommendations issued by the monitoring device may be presented in addition to the indications derived from the PI. Examples of such analysis of waveform pattern may be found in publication: Krause B. and Hess D. R. (2007) "Capnography for procedural sedation and analgesia in the emergency department", Ann Emerg Med. 50(2), Pages 172-81, incorporated herein by reference. For example, lower airway obstruction may be seen by a capnogram showing a curved ascending phase and up-sloping alveolar plateau that indicate the presence of acute bronchospasm or obstructive lung disease; for example, distinguishing between bradypneic hypoventilation from hyperventilation may be performed according to the CO2 wave form: while in the bradypneic hypoventilation decreased respiratory rate, high amplitude and wide capnogram are detected, in hyperventilation an increase in respiratory rate, low amplitude and narrow capnogram are detected.

According to some embodiments, the medical device may further include a user interface that may allow the user to select the data to be displayed and to control various operating parameters. Moreover, different displays may be included to accommodate different needs of the different users (such as a nurse, a physician, an anesthesiologist, and the like). Allowing the user to change the view of the data may permit the user to toggle through the different levels of information for further evaluation of a condition. For example, the basic screen may display the condition-index-value and the condition-index-value trend data. Changing to the next display may reveal the actual (measured) data values and the trends of the values that relate to the parameters from which the condition-index-value is determined/calculated. Further toggling the display may provide the pause frequency and other related analysis and calculation. The use of the various displays may also allow the user to focus on the parameters that caused an indication of an event and/or recommendation to the user.

According to further embodiments, the user interface may also allow the user to enter information that is characteristic for each patient. The use of characteristic patient information is necessary to allow accuracy of the various measurements and calculations. Such information may include, for example, age, weight, height, sex, and the like, of the specific patient, as well as other patient related information, such as, intubation (if the patient is intubated or not). For example, the patient size and age may change the PI calculations: for an adult a respiration rate of 12 BPM would be normal, but 36BPM would be considered high, whereas for a child, respiration rate of 12 may be considered low, while 36BPM may be considered normal. In addition, classification detection means of various patients may be utilized, wherein the classification may be based on parameters such as, for example, age group, weight group, sex, intubation, and the like. Using such classification may allow the monitoring device to correct its settings to be appropriate for that relevant patient type and environment. In addition, the user interface may allow automatic detection of the type of the patient according to the measuring interface being used. For example, a tubing interface used to measure $CO_2$ in breath may be different between an adult and a child and accordingly, the user interface may automatically adjust the patient settings to match the patient size group.

Reference is now made to FIG. 6, which illustrates exemplary graphical user interfaces, according to some embodiments. As shown in FIG. 6A, user interface display 200 may display one or more elements, which are related to the determined/calculated index. The content of what is to be displayed may be determined by a user. For example, display 200, may include element 202, which may allow the user to select a designated display and to further indicate which display is selected. Element 204 may display the value of the determined/calculated PI. Element 206 may display the trend (change over time) of the determined/calculated PI. Element 208 may include graphical indications as to the changes of the value of the PI. Element 210 may illustrate the values of one or more of the parameters that are used to determine the index value. Element 212 may illustrate the trend of one or more of the parameters that are used to determine the index value. Element 214 may be used to present medical recommendation to a health care provider. The display of the various elements may include any type of display, such as, for example, a numerical value display, a graph display, a chart, a table, a graphical indication display, a colored-index display, and the like. Reference is now made to FIG. 6B, which illustrates an exemplary graphical display of a PI index, according to some embodiments. As shown in FIG. 6B, graphical user interface, 250, may display various elements. For example, element 252 may allow the user to select a designated display and to further indicate which display is selected. For example, the various displays may include, trend, system, patient type, alarms, print, zoom, and the like. Element 254 may include a numerical display of the PI value. Element 258 may include a graphical indication (such as, for example, an arrow) of the change in the PI. Element 256 may include a display of the trend of the index over a selected period of time, such as for example, 2 hours. The trend display may be, for example, in the form of a graph which depicts the changes in the PI value over time. Elements 260A-D may display values of various parameters where, according to at least some of them, the PI is determined/calculated. For example, as shown in FIG. 6B, element 260A displays the level of EtCO2 (in units of mmHg) as a numerical value. For example, element 260B illustrates the respiratory rate (RR, in units of respirations per minute) as a numerical value. For example, element 260C illustrates the SpO2 levels (% saturation) as a numerical value. For example, element 260D illustrates the Heart rate (HR, units of pulses per minute) as a numerical value. In addition, elements 262 A-D are graphical indicators of the changes of the various parameters. For example, elements 262A-D may be in the form of an up-facing and/or down facing arrow. Element 264 may further illustrate a graph depicting CO2 waveform (in units of mmHg). Reference is now made to FIG. 6C, which illustrates an exemplary graphical display of a PI index, according to some embodiments. As shown in FIG. 6C, graphical user interface 300 may display the trend (change over time) of various elements, such as, for example, a PI value, various parameters used to determine the index value, and the like. The selected time period over which the trend is observed may include any time period, such as, for example, 0.1 to 24 hours. The time period may be selected by a user and/or may be automatically determined. For example, the time period for displaying the trend may be 6 hours. For example, element 304 may include a numerical display of the PI value. For example, element 305 may include a graph display of the trend of the PI value over a selected time period. For example, element 306 may include a numerical display of the heart rate parameter. For example, element 307 may include a graph display of the trend of the heart rate parameter value over a selected time period. For example, element 308 may include a numerical display of the $SpO_2$ parameter. For example, element 309 may include a graph display of the trend of the $SpO_2$ parameter value over a selected time period. For example, element 310 may include a numerical display of the respiratory rate parameter. For example, element 311 may include a graph display of the trend of the respiratory rate parameter value over a selected time period. For example, element 312 may include a numerical display of the $EtCO_2$ parameter. For example, element 313 may include a graph display of the trend of the $EtCO_2$ parameter value over a selected time period. According to some embodiments, regions of each individual trend may be shaded, so that the deviations from "normal" regions of the trend are easily distinguished. In addition, or alternatively, the graph may change in color (for example to yellow and/or red) for those regions that are out of the normal region. Reference is now made to FIG. 6D, which illustrates an exemplary graphical display of a PI index, according to some embodiments. As shown in FIG. 6D, graphical user interface, 350, may display the frequency of events wherein deviations from alarm limits (threshold) have been detected over a period of time. Displaying the frequency of events may include numerical values, graph display, color-coded display, and the like, or any combination thereof. For example, element 352 illustrates a bar graph showing the number of times where the respiratory rate was above a high alarm limit (top panel, 353A) or below a low alarm limit (bottom panel, 353B). For example, element 354 illustrates a bar graph showing the number of times where the SpO2 value was above a high alarm limit (top panel, 355A) or below a low alarm limit (bottom panel, 355B). For example, element 356 illustrates a bar graph showing the number of times where the EtCO2 value was above a high alarm limit (top panel, 357A) or below a low alarm limit (bottom panel, 357B). For example, element 358 illustrates a bar graph showing the number of times where the heart rate was below a high alarm limit (top panel, 359A). For example, element 360 illustrates a bar graph showing the number of times where the PI value was below a low alarm limit (top panel, 361A). The time period over which the frequency of events is determined may be automatically determined and/or may be determined by the user. In addition to displaying the frequency of events, graphical user interface 350 may further display graph and/or numerical display of any parameter and/or value. For example, element 362 may display the instantaneous measured value of $EtCO_2$. For example, element 364 may display the instantaneous measured value of the respiration rate. For example, element 368 may display the instantaneous measured value of the $SpO_2$. For example, element 370 may display the instantaneous measured value of the heart rate.

According to some embodiments, there is thus provided a medical device (and system) that may be used to monitor a patient's health condition, such as respiratory and/or pulmonary and/or cardiac status. The device may include, for example a capnography device that may be adapted to sense and/or obtain measurements of various parameters in addition to $CO_2$. Such parameters may include, for example, $O_2$ levels, $O_2$ partial pressure, such as SpO2, heart rate, blood pressure, and the like. The device may further include a processing logic that may be used to receive information from at least one of the sensors and to compute/determine/generate a condition-index-value that is directly related to a condition of the patient. The processing logic may include any type of hardware and/or software, such as, for example, a processor. The condition index value may be in the range of 1 to 10, wherein 10 indicates the best condition while 1 indicates the worst condition. The monitoring device may further include one or more display that may be used to present the data collected and determined/calculated by the monitoring device. The display may present, for example, the determined/calculated condition index in numerical format and in indexed format, wherein different ranges along the 1-10 scale of the determined/calculated index may be assigned different colors; the change (trend) of the determined/calculated condition index value over time; the reliability of the determined/calculated index value; values and patterns of the various parameters measured by the various sensors of the monitoring device; graphical indications regarding the status of the patient, such as, for example, downward and upward arrows; and the like. The monitoring device may further be adapted to issue medical recommendations based upon the determined/calculated condition index value and other measured patient parameters. In addition, the monitoring device may include a user interface that may allow the user to input patient related data that is specific for the patient, such as, for example, age, sex, and/or size of the patient. The user interface may further allow the user to choose the parameters to be displayed and the form in which the parameters may be displayed, such as, for example, in the form of graphs, numerical values, indicators, and the like.

Figure 7:
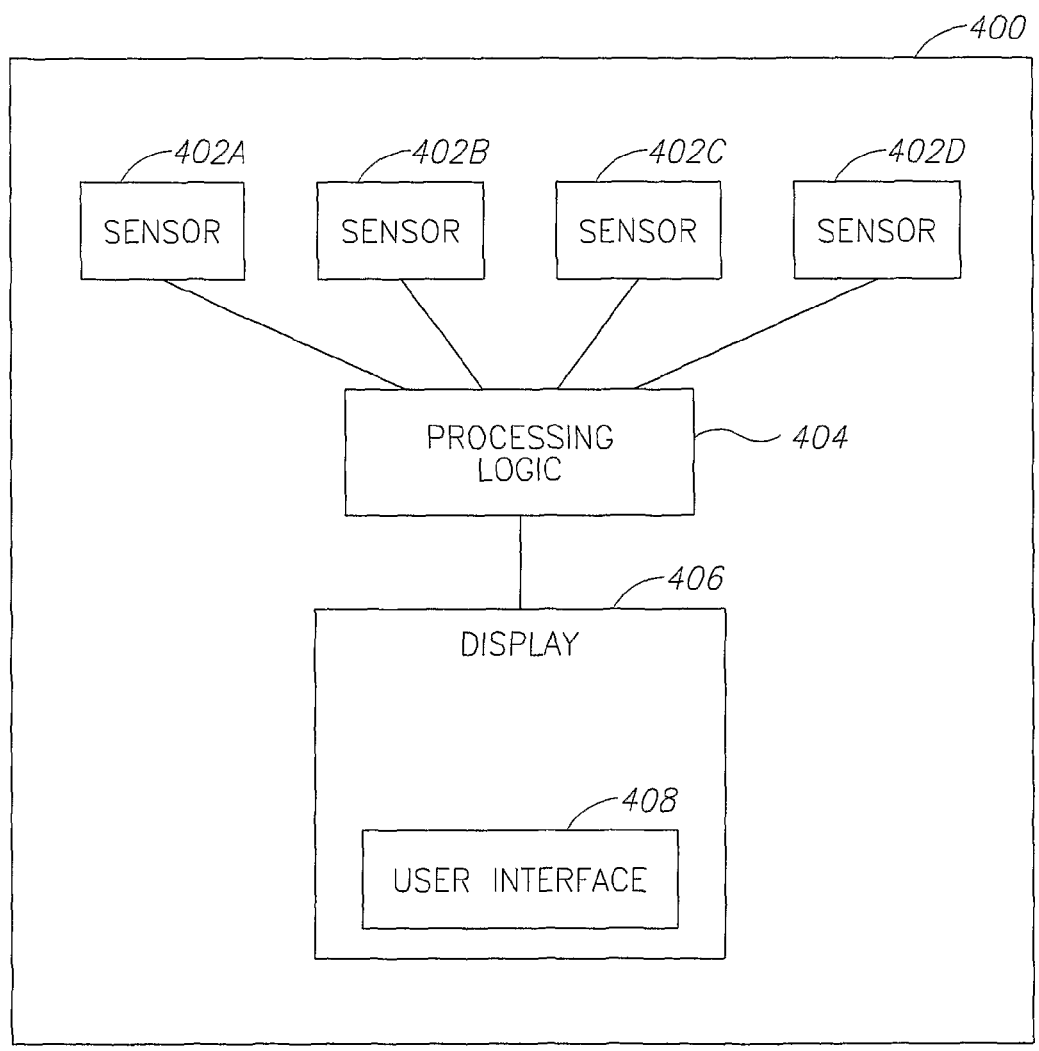
FIG. 7—A block diagram of a medical monitoring system, according to some embodiments.

Reference is now made to FIG. 7, which illustrates a block diagram of a medical monitoring system, according to some embodiments. As shown in FIG. 7, medical monitoring system 400 may include one or more sensors, such as, for example, sensors 402A-D that may be adapted to obtain/sense/measure various health related parameters. The sensors may include such sensors as, for example, but not limited to: capnograph, oximeter, spirometer, heart rate sensors, blood pressure sensors, ECG, EEG, Ultrasound, and the like. The parameters thus measured may include, for example, such parameters as, but not limited to: $EtCO_2$, $CO_2$ levels, $SpO_2$, heart rate, blood pressure, flow, $CO_2$ waveform pattern, blood gases, and the like. Medical monitoring system 400 may further include a processing logic, such as, for example, processing logic 404, that may be used to receive information from at least one of the sensors and to compute/determine/generate a condition-index value that is directly related to a condition of the patient. For example, the condition index value may be a Pulmonary/Respiratory index. The processing logic may include any type of hardware and/or software, such as, for example, a processor. The connection between the processing logic and the sensor(s) may include any type of communication route, such as, for example, use of wires, cables, wireless, and the like. The medical monitoring system may further include one or more displays (such as, for example, display 406 in FIG. 7) that may be used to present the data collected and determined/calculated/computed by the processing logic, such as, for example, the index value, the index trend, the parameters used to determine the index, and the like. In addition, the medical monitoring system may further include a user interface, such as user interface 408 that may allow the user to input patient related data that is specific for the patient, such as, for example, age, gender, weight, height, medical history, current medical status, and the like, or any combination thereof. The user interface may further allow the user to choose the parameters to be displayed and the form in which the parameters may be displayed.

Figure 8:
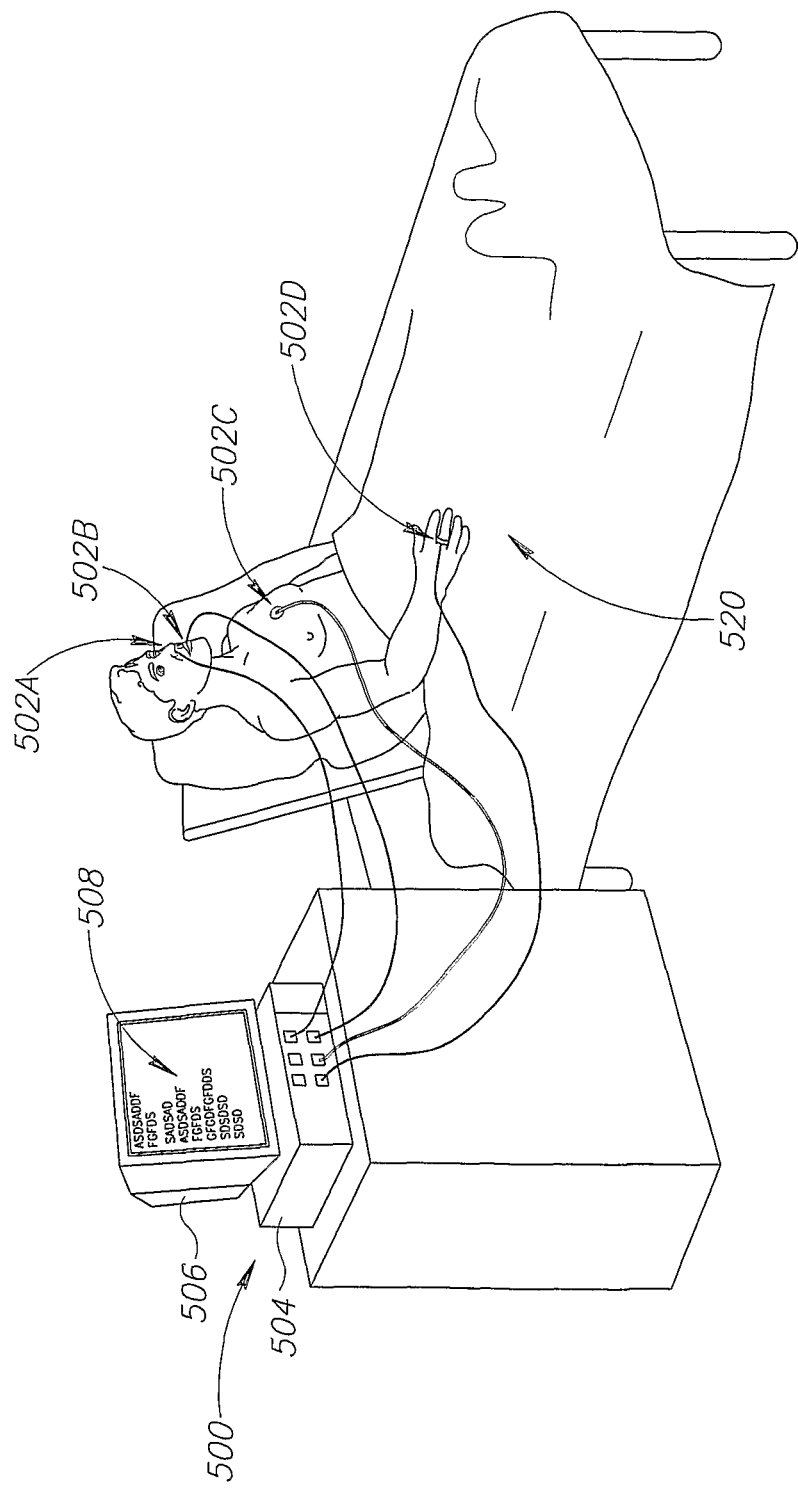
FIG. 8—A schematic illustration of a system, according to some embodiments.

Reference is now made to FIG. 8, which illustrates a schematic illustration of a system, according to some embodiments. As shown in FIG. 8, a system, such as medical monitoring system 500, may include one or more sensors, such as, for example, sensors 502A-D that may be adapted to obtain/sense/measure various health related parameters. The one or more sensors may be connected directly or indirectly to a patient (such as patient 520). The sensors may include such sensors as, for example, but not limited to: capnograph, oximeter, spirometer, heart rate sensors, blood pressure sensors, ECG, EEG, Ultrasound, and the like. The parameters thus measured may include, for example, such parameters as, but not limited to: $EtCO_2$, $CO_2$ levels, $SpO_2$, heart rate, blood pressure, flow, $CO_2$ waveform pattern, blood gases, and the like. System 500 may further include a processing logic, such as, for example, processing logic 504, that may be used to receive information from at least one of the sensors and to compute/determine/generate a condition-index value that is directly related to a condition of the patient. For example, the condition index value may be a Pulmonary/Respiratory index. The processing logic may include any type of hardware and/or software. The connection between the processing logic and the sensor(s) may include any type of communication route, such as, for example, use of wires, cables, wireless, and the like. The medical monitoring system may further include one or more displays (such as, for example, display 506 in FIG. 8) that may be used to present the data collected and determined by the processing logic, such as, for example, the index value, the index trend, the parameters used to determine the index, and the like. In addition, the medical monitoring system may further include a user interface, such as, user interface 508 that may allow the user to input patient related data that is specific for the patient, such as, for example, age, gender, weight, height, medical history, current medical status, and the like, or any combination thereof. The user interface may further allow the user to choose the parameters to be displayed and the form in which the parameters may be displayed.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

EXAMPLES

Example 1

Calculating PI Value Using Mathematical Methods

As detailed hereinabove, any of the parameter values used for the calculation of the PI is based on the determined/calculated/computed value of the average $EtCO_2$, average respiratory rate, average heart rate and average $SpO_2$.

$EtCO_2$—End tidal $CO_2$ is measured in units of mmHg
RR—Respiration Rate is measured in number of breaths per minute
$SpO_2$—is measured in percentile
HR—Heart Rate is measured in pulses per minute The examples below illustrates index value at various conditions.

PI≥9-10

When the following conditions are realized, the index will be 10 or 9 and no arrows indicative of hyper or hypoventilation, are displayed:

The following conditions are interpreted as follows: If the respiration rate is in the range of 12 to 28 BPM, and End tidal CO2 is equal to or higher than 28 and smaller that 44 mmHg and SpO2 is higher that 94%, then the determined/calculated/computed index is 10. If the Respiration rate is in the range of 12 to 28 BPM and End tidal CO2 is equal to or above 28 and lower than 44 and SpO2 is in the range of 90 to 94%, then the determined/calculated/computed index is 9. Those conditions may be summarized as follows:

| | | |
|---|---|---|
| If RR is >12 & <28 And EtCO2 ≥28 & <44 And SpO2 >94% | Then: | Index = 10 |
| If RR is >12 & <28 And EtCO2 ≥28 & <44 And SpO2 >90% & <94% | Then: | Index = 9 |

PI≤7 and Indication of Hypoventilation

| | | |
|---|---|---|
| If RR is ≤5 If RR is ≤8 And EtCO2 ≥64 Or EtCO2 ≤12 Or SpO2 ≤86% | Then: | Index = 4 down |
| If RR is ≤5 And EtCO2 ≥64 Or EtCO2 ≤12 | Then: | Index = 3 down |
| And SpO2 ≤86% If RR is ≤5 | Then: | Index = 1 down |
| And SpO2 ≤86% If RR is >5 & ≤8 And EtCO2 ≥46 & <64 Or EtCO2 ≤24 & >12 | Then: | Index = 2 down |
| And SpO2 ≤90% & >86% If RR is >5 & ≤8 And EtCO2 ≥46 & <64 Or EtCO2 ≤24 & >12 | Then: | Index = 5 down |
| And SpO2 >90% If RR is >8 & ≤12 And EtCO2 ≥55 Or EtCO2 <18 | Then: | Index = 6 down |
| And SpO2 ≤90% If RR is >8 & ≤12 And EtCO2 ≥55 Or EtCO2 <18 | Then: | Index = 6 down |
| And SpO2 >90% | Then: | Index = 7 down. |

PI≤8 and No Indication of Hyperventilation or Hypoventilation:

| | | |
|---|---|---|
| If RR is >12 & <16 And $EtCO_2$ ≥64 Or EtCO2 <12 And SpO2 <90% | Then: | Index = 6 |
| If RR is >12 & <16 And $EtCO_2$ ≥64 Or $EtCO_2$ <12 And $SpO_2$ >90% | Then: | Index = 7 |
| If RR is >12 & <16 | | |

-continued

| | | | |
|---|---|---|---|
| And EtCO2 ≥44 & <64 | | | |
| Or EtCO2 ≤24 & >12 | | | |
| And SpO2 <90% | Then: | Index = 7 | |
| If RR is >12 & <16 | | | |
| And EtCO2 ≥44 & <64 | | | |
| Or EtCO2 ≤24 & >12 | | | |
| And SpO2 >90% | Then: | Index = 8 | |

PI≤8 and Indication of Hyperventilation

| | | | |
|---|---|---|---|
| If RR is ≥40 | | | |
| And HR is ≥110 | Then: | Index = 4 Up | |
| If RR is ≥40 | | | |
| And EtCO2 ≥50 | | | |
| And HR is ≥110 | Then: | Index = 3 Up | |
| If RR is ≥40 | | | |
| And EtCO2 ≥50 | | | |
| And HR is ≥110 | | | |
| And SpO2 ≤90% | Then: | Index = 2 Up | |
| If RR is ≥40 | | | |
| And EtCO2 ≥44 & <50 | | | |
| And HR is ≥100 | | | |
| And SpO2 ≤90% | Then: | Index = 3 Up | |
| If RR is ≥40 | | | |
| And EtCO2 ≥44 & <50 | | | |
| And HR is ≥100 | | | |
| And SpO2 >90% | Then: | Index = 4 Up | |
| If RR is ≥32 & <40 | | | |
| And HR is ≥100 | Then: | Index = 8 Up | |
| If RR is ≥32 & <40 | | | |
| And HR is ≥100 & <120 | | | |
| And EtCO2 ≥44 & <50 | Then: | Index = 7 Up | |
| If RR is ≥32 & <40 | | | |
| And HR is ≥100 | | | |
| And EtCO2 ≥44 | | | |
| And SpO2 ≤90% | Then: | Index = 6 Up | |
| If RR is ≥32 & <40 | | | |
| And HR is ≥120 | | | |
| And EtCO2 ≥55 | Then: | Index = 5 Up | |
| If RR is ≥28 & <32 | | | |
| And HR is ≥120 | | | |
| And EtCO2 ≥55 | Then: | Index = 6 Up | |
| If RR is ≥28 & <32 | | | |
| And HR is ≥100 | | | |
| And EtCO2 ≥44 | Then: | Index = 7 Up | |
| And EtCO2 ≥44 & <64 | | | |
| Or EtCO2 ≤24 & >12 | | | |
| And SpO2 <90% | Then: | Index = 7 up | |
| If RR is >16 & <28 | | | |
| And EtCO2 ≥44 & <64 | | | |
| Or EtCO2 ≤24 & >12 | | | |
| And SpO2 <90% | Then: | Index = 7 up | |

Example 2

Determining PI Value Using Mathematical Methods—Fuzzy Logic Algorithm

A fuzzy logic inference is built using expert health care providers' knowledge and interpretation on anticipated PI values given four parameters: $EtCO_2$, Respiratory Rate (RR), Heart Rate (HR) and $SpO_2$. Since there are differences in the normal ranges of HR and RR between adults and children at different ages, the PI values for the same parameters may differ. Hence PI-models are designed for distinct ages. The following descriptions apply to all modes, however the details are of adult mode.

In order to determine the PI value based on the four parameters (EtCO2, RR, HR and SpO2), a questionnaire is sent to 22 medical experts (nurses, respiratory therapists, doctors and anesthesiologists). The questionnaire includes a set of 85 cases with different parameters values. The experts are asked to assign a PI value according to a predefined code (Table 1).

| PI Value | Implication |
|---|---|
| 10 | Perfectly healthy normal |
| 8 to 9 | Normal |
| 7 | Understandable but requires more attention |
| 5 to 6 | It is recommended to pay more attention |
| 3 to 5 | Requires more attention and intervention is recommended |
| 1 to 3 | Requires intervention |

Fuzzy logic inference is built using the consensus of experts' data. The design is carried out using matlab fuzzy logic toolbox (Mathworks Inc.). Initially, membership functions are assigned for each parameter, determining the ranges for: Normal, High and Low values for HR and $SpO_2$ and Normal, High, Very-High, Low and Very-Low for $EtCO_2$ and RR. The PI has ten membership functions, one for each index value.

A rule set is determined relating the inputs to the output, using the verbal descriptor of the membership functions (for example, if ($ETCO_2$ is Very High) and (RR is Very High) and ($SpO_2$ is Normal) and (HR is High) then (PI is 2)). The rules are summarized in a table 2.

| | RR | | | | |
|---|---|---|---|---|---|
| EtCO2 | VH | H | N | L | VL |
| VH | 3 | 5 | 4 | 3 | 2 |
| H | 7 | 8 | 7 | 5 | 3 |
| N | 7 | 8 | 10 | 7 | 6 |
| L | 5 | 6 | 8 | 4 | 2 |
| VL | 3 | 3 | 4 | 2 | 2 |

SpO2 N, HR N
SpO2 L → I = I-1
SpO2 VL → I = 1
HR L → I = I-2
HR H → I = I-1

The fuzzy logic operators used are: min for AND, max for OR, max for Aggregation and centroide of area for de-fuzzification.

The examples described above are non-limiting examples and are not intended to limit the scope of the disclosure. The described examples may comprise different features, not all of which are required in all embodiments of the disclosure.

What is claimed is:

1. A system for weaning a patient from mechanical ventilation (MV), the system comprising: a ventilation device; and a controller comprising an interface module configured to receive two or more measured patient parameters, wherein at least one of the two or more measured patient parameters comprises a $CO_2$ related parameter, wherein said controller is further configured to compute an Integrated Pulmonary Index (IPI) value based on the two or more measured patient parameters and to provide a signal to said ventilation device, based on the computed IPI value, wherein said signal adjusts one or more weaning related parameters in said ventilation device; wherein the IPI is computed by:
    (a) characterizing a first measured patient parameter of the two or more measured patient parameters based on a comparison of the first measured patient parameter against a first reference value;

(b) characterizing a second measured patient parameter of the two or more measured patient parameters based on a comparison of the second measured patient parameter against a second reference value; and (c) computing the IPI value based on values associated with each of the characterized first and second measured patient parameters, wherein a weighting factor applied to the value associated with the second characterized measured patient parameter is influenced by the characterization of the first measured patient parameter.

2. The system according to claim 1, wherein the one or more weaning related parameters comprise: ventilation volume, ventilation pressure, supplemental oxygen, positive end expiratory pressure (PEEP) or any combination thereof.

3. The system according to claim 1, wherein adjusting one or more weaning related parameters in said ventilation device includes reducing or stopping the mechanical ventilation if the IPI value is at or above a predetermined value or continuing or increasing the support of the mechanical ventilation if the IPI value is below the predetermined value.

4. The system according to claim 1, wherein adjusting one or more weaning related parameters in said ventilation device includes reducing or stopping supplemental oxygenation if the IPI value is at or above a predetermined value or continuing or increasing the supplemental oxygenation if the IPI value is below the predetermined value.

5. The system according to claim 1, wherein adjusting one or more weaning related parameters in said ventilation device includes reducing or stopping positive end expiratory pressure (PEEP) if the IPI value is at or above a predetermined value or continuing or adding PEEP if the IPI value is below the predetermined value.

6. The system according to claim 1, wherein the IPI is in the range of 1 to 10, wherein the higher the IPI value, the better the patient condition is.

7. The system according to claim 1, wherein an increase in the IPI value is indicative of a better chance a patient has for a successful weaning.

8. The system according to claim 1, wherein an increase in the IPI value or stabilization thereof is indicative of a successful weaning process.

9. The system according to claim 1, wherein a decrease in the IPI value is indicative of a deterioration of a patient's condition.

10. The system according to claim 1, wherein the controller is further configured to compute a trend of the IPI value and to provide a signal to said ventilation device, based on the trend of the IPI value, wherein said signal adjusts one or more weaning related parameters in said ventilation device.

11. The system according to claim 1, wherein the controller is further configured to compute a reliability index of the [index-value] IPI value.

12. The system according to claim 1, wherein the controller is further configured to provide a medical recommendation regarding weaning from the ventilation machine.

13. The system according to claim 12, further comprising a graphical display configured to display at least one of the IPI value or the recommendation regarding weaning from the ventilation machine.

14. The system according to claim 1, wherein computing the IPI comprises applying a fuzzy logic, a Bayesian network, a decision tree, a neural network, a radial base function, a linear regression model, a non-linear regression model, an expert system, or any combination thereof.

15. The system according to claim 1, wherein computing the IPI comprises averaging the first measured patient parameter[s] over a first period of time and averaging the second measured patient parameter over a second period of time.

16. The system according to claim 15, wherein the period of time is determined based on one or more patient characteristics, on the stability of one or more of the two or more measured patient parameters or both.

17. The system according to claim 1, wherein the two or more measured patient parameters comprise a $CO_2$ related parameter and one or more measured patient parameters selected from the group consisting of: another $CO_2$ related parameter, respiration rate (RR), an $O_2$ related parameter, heart rate (HR), an electrocardiogram (ECG), an encephalogram (EEG), blood pressure, and spirometry.

18. The system according to claim 1, wherein the $CO_2$ related parameter comprises a $CO_2$ waveform related parameter, an expired air $CO_2$ concentration, respiratory rate or any combination thereof.

19. The system according to claim 18, wherein the $CO_2$ waveform related parameter comprises $EtCO_2$, changes in $EtCO_2$, a slope of the increase in the $CO_2$ concentration, a change in a slope of the increase in the $CO_2$ concentration, time to rise to a predetermined percentage of a maximum value of $CO_2$ concentration, a change in time to rise to a predetermined percentage of a maximum value of $CO_2$ concentration, an angle of rise to a predetermined percentage of a maximum value of $CO_2$ concentration, a change in an angle of rise to a predetermined percentage of a maximum value of $CO_2$ concentration, breath to breath correlation, breath to breath correlation, a $CO_2$ duty cycle, a change in $CO_2$ duty cycle or any combination thereof.

20. The system according to claim 1, wherein computing comprises applying a learning process, wherein the learning process increases reliability of the index value.

21. The system according to claim 20, wherein the learning process comprises neural network methods, a support vector machine (SVM), genetic algorithms, simulated annealing, expectation-maximization (EM), case based reasoning, or any combination thereof.

22. The system according to claim 1, wherein computing the IPI is based on the two or more measured patient parameters and on one or more patient characteristics.

23. The system according to claim 22, wherein the one or more patient characteristics comprises age, weight, gender, medical condition, medication, ventilation, oxygen supply, lab tests results, blood pressure, medical history, intubation or any combination thereof.

24. The system according to claim 23, wherein the medical history comprises smoking, heart disease, lung disease, sleep apnea, a pacemaker, or any combination thereof.

* * * * *